United States Patent
Reiffenrath et al.

(10) Patent No.: US 7,790,929 B2
(45) Date of Patent: Sep. 7, 2010

(54) CHIRAL PHENOL DERIVATIVE, LIQUID CRYSTAL MEDIUM CONTAINING SAID CHIRAL PHENOL DERIVATIVE

(75) Inventors: Volker Reiffenrath, Roβdorf (DE); Michael Heckmeier, Hemsbach (DE)

(73) Assignee: Merck Patent GmbH, Darmstadt (DE)

( * ) Notice: Subject to any disclaimer, the term of this patent is extended or adjusted under 35 U.S.C. 154(b) by 154 days.

(21) Appl. No.: 10/530,572

(22) PCT Filed: Sep. 18, 2003

(86) PCT No.: PCT/EP03/10398

§ 371 (c)(1), (2), (4) Date: Apr. 7, 2005

(87) PCT Pub. No.: WO2004/033406

PCT Pub. Date: Apr. 22, 2004

(65) Prior Publication Data

US 2006/0011888 A1     Jan. 19, 2006

(30) Foreign Application Priority Data

Oct. 7, 2002    (DE) .............................. 102 46 657

(51) Int. Cl.
*C07C 43/23* (2006.01)
*C07C 39/367* (2006.01)
*C07C 39/06* (2006.01)
*C09K 19/58* (2006.01)

(52) U.S. Cl. ...................... 568/362; 568/642

(58) Field of Classification Search ................ 568/642
See application file for complete search history.

(56) References Cited

U.S. PATENT DOCUMENTS

| | | | | |
|---|---|---|---|---|
| 4,038,250 A | * | 7/1977 | Lind | 524/291 |
| 4,067,895 A | * | 1/1978 | Hofer et al. | 554/65 |
| 4,758,501 A | * | 7/1988 | Buckland et al. | 430/389 |
| 4,826,620 A | * | 5/1989 | Heppke et al. | 252/299.61 |
| 5,487,893 A | * | 1/1996 | Vachy | 424/539 |
| 6,444,278 B1 | | 9/2002 | Reiffenrath et al. | |

FOREIGN PATENT DOCUMENTS

| | | |
|---|---|---|
| DE | 19539141 | 4/1997 |
| DE | 10117224 | 2/2002 |
| EP | 0217239 | 4/1987 |

OTHER PUBLICATIONS

Schwartz, L., Flor, R., Gullo, V., "A Reinvestigation of the direction of acid-catalyzed ring opening of substituted spirocyclopropylcyclohexadienones", J. Org. Chem. 1974, 39(2), 219-222.*

Maeurer, M. et al.: "Stereoelectronic and Steric Effects in the Synthesis and Recognition of Diastereomeric Ethers by NMR and EPR Spetroscopy" Chemische Berichte, 125(4), 857-65 CODEN: CHBEAM; ISSN: 0009-2940, 1992.

* cited by examiner

*Primary Examiner*—Daniel M Sullivan
*Assistant Examiner*—Yevegeny Valenrod
(74) *Attorney, Agent, or Firm*—Millen, White, Zelano & Branigan, P.C.

(57) ABSTRACT

The invention relates to chiral phenols, preferably of formula (I), the different parameters having the meaning indicated in the description, liquid crystal media which contain said compounds as chiral doping agents and/or stabilizers, and the use thereof in electro-optical displays.

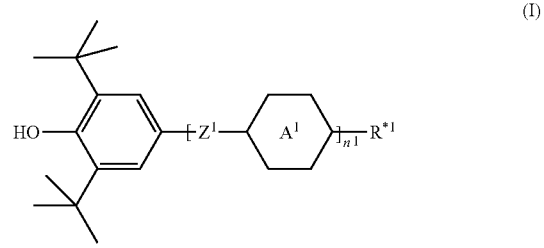

31 Claims, No Drawings

CHIRAL PHENOL DERIVATIVE, LIQUID CRYSTAL MEDIUM CONTAINING SAID CHIRAL PHENOL DERIVATIVE

The present invention relates to chiral phenol derivatives and to liquid-crystalline media which comprise these compounds. The present invention also relates to a process for the chiral doping and simultaneous stabilisation of liquid-crystal mixtures. The present invention furthermore relates to liquid-crystal displays which contain the liquid-crystal mixtures according to the invention.

In the known liquid-crystal displays, the liquid crystals, generally liquid-crystalline mixtures, are used as dielectrics whose optical properties change reversibly on application of an electric voltage. These liquid-crystal displays use various electro-optical effects. The commonest of these are the TN (twisted nematic) effect, with a homogeneous, virtually planar initial alignment of the liquid crystals and a nematic structure twisted by about 90°, the STN effect (supertwisted nematic) and the SBE effect (super-twisted birefringence effect), both of which, like the TN effect, use a twisted, homogeneous initial alignment of the liquid crystals, but here the molecules have a significant surface tilt angle ("tilt angle" for short) at the surface of the substrates, and the twist between the substrates is significantly greater than 90°. In this application, unless explicitly stated otherwise, the STN effect and the SBE effect below are both jointly referred to as the STN effect. The tilt angle at the surface in STN displays is typically between 2° and 10°. It is greater the greater the twist angle. The twist angles are generally about 180° to 240°, sometimes also up to 260° or 270° and in some cases even greater.

The twist of the liquid-crystal medium by greater than 90° is achieved through the use of chiral liquid-crystal mixtures whose natural twist is selected in accordance with the layer thickness of the liquid-crystal layer. To this end, two possibilities are available to the person skilled in the art. The first consists in the use of liquid crystals which are themselves chiral, i.e. cholesteric liquid crystals. Such liquid crystals themselves have a twisted structure. In a homogeneously aligned arrangement between two substrates, which is known as the Grandjean texture, the director of the molecules is helically twisted in the vertical direction, i.e. over the thickness of the layer.

The characteristic length for a complete rotation through 360° is known as the cholesteric pitch (P). However, the use of cholesteric liquid crystals is often not particularly advantageous since the cholesteric pitch of cholesteric liquid crystals cannot be matched easily to the layer thicknesses of the display cells usually used. In addition, the cholesteric pitch of these liquid crystals is often disadvantageously and in many cases highly dependent on the temperature. A change in the composition of the mixtures also usually results in considerable changes in the cholesteric pitch.

For this reason, in most practical cases a chiral substance which induces the desired twist is added to a nematic liquid-crystal mixture. It is not particularly important here whether this compound itself has a mesophase. Rather, it is more important that it has a high twisting power for the nematic base mixture (also known as host mixture) and that it does not change the properties of the base mixture, in particular its clearing point, excessively in the concentrations usually employed. Preference is thus generally given to the use of compounds which themselves have a mesogenic structure or are even cholesteric.

The cholesteric phases which are induced by addition of chiral substances to nematic liquid crystals are often known as chirally nematic phases. In the present application, however, these are also referred to as cholesteric phases, unless explicitly stated otherwise.

The cholesteric pitch induced by addition of chiral substances (dopants) to nematic liquid crystals is dependent at a given temperature, besides on the enantiomeric purity of the chiral dopant, in particular on the dopant concentration (c) employed and on the twisting power of the dopant. This twisting power is known as the HTP (helical twisting power). To a first approximation, the induced cholesteric pitch (P) is inversely proportional to the product of HTP and dopant concentration employed, as shown in equation (1).

$$P = (HTP \cdot c)^{-1} \qquad (1)$$

In STN displays, use is typically made of liquid-crystal mixtures having a cholesteric pitch to layer thickness ratio (d/P) in the range from 0.4 to 0.8, frequently of about 0.5.

However, chiral liquid-crystal mixtures are also used in TN displays, here in order to avoid twist in the reverse direction (reverse twist). Occurrence of this would result in the formation of domains and thus in a reduction in contrast. In TN displays, use is generally made of cholesteric liquid-crystal mixtures having a significantly smaller d/P ratio than in STN displays since larger d/P values in most cases result in an increase in the threshold voltage. The values here are typically about 0.01 to 0.3, frequently about 0.1.

Besides these display types, there are further liquid-crystal displays which use liquid-crystal mixtures doped with chiral compounds.

Known chiral dopants are, for example, the compounds C15, CB15, R-811 and S-811, R-1011 and S-1011, and R-2011 and S-2011, all Merck KGaA.

In these and similar electro-optical effects, use is made of liquid-crystalline media of positive dielectric anisotropy ($\Delta\epsilon$).

Besides the electro-optical effects mentioned which require liquid-crystal media of positive dielectric anisotropy, there are other electro-optical effects which use liquid-crystal media of negative dielectric anisotropy, such as, for example, the ECB (electrically controlled birefringence) effect and its sub-forms DAP (deformation of aligned phases), VAN (vertically aligned nematics) and CSH (colour super homeotropics). In these and similar electro-optical effects, use is made of liquid-crystalline media of negative dielectric anisotropy ($\Delta\epsilon$).

An electro-optical effect having excellent, low viewing-angle dependence of the contrast uses axially symmetrical micropixels (ASMs). In this effect, the liquid crystal of each pixel is surrounded cylindrically by a polymer material. This mode is particularly suitable for combination with addressing through plasma channels. In particular, large-area PA LCDs having good viewing-angle dependence of the contrast can be achieved in this way.

The IPS (in plane switching) effect employed to an increased extent recently can use both dielectrically positive and dielectrically negative liquid-crystal media, similar to guest-host displays, which can employ dyes either in dielectrically positive or in dielectrically negative media, depending on the display mode used.

The pixels of the liquid-crystal displays can be addressed directly, time-sequentially, i.e. in time-multiplex mode, or by means of a matrix of active, electrically non-linear elements.

The commonest AMDs (active matrix displays) hitherto use discrete active electronic switching elements, such as, for example, three-pole switching elements, such as MOS (metal oxide silicon) transistors or thin-film transistors (TFTs) or varistors or 2-pole switching elements, such as, for example, MIMs (metal insulator metal) diodes, ring diodes or back-to-back diodes. In the TFTs, various semiconductor materials, predominantly silicon or alternatively cadmium selenide, are used. In particular, amorphous silicon or polycrystalline silicon is used.

Some liquid-crystalline compounds and some mesogenic compounds having otherwise technically favourable properties are not sufficiently stable for use in practical liquid-crystal displays. There are various reasons for the inadequate stability of the various compounds. These may be due to inadequate stability of the compounds to UV radiation and/or visible light or to their inadequate stability to thermal loads.

Some compounds react with even traces of oxygen. This takes place faster at higher temperatures. In the case of liquid-crystal mixtures which comprise compounds of this type, the stability to thermal loads, and thus the life of the displays, can be significantly increased by adding corresponding stabilisers.

Thus, DE 195 391 41 and DE 101 172 24 propose a phenol of the formula

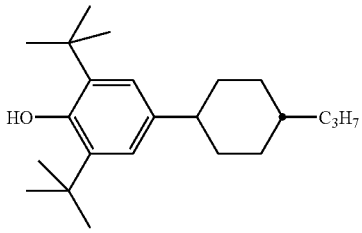

as stabiliser for liquid-crystal mixtures of this type. These compounds are not chiral and are thus not suitable for inducing a cholesteric phase in nematic liquid crystals.

If it is intended to use liquid-crystal mixtures which compounds having relatively low stability to thermal loads in the presence of oxygen in displays which require cholesteric liquid crystals, both a chiral dopant and a stabiliser must be added to the nematic base mixtures. This means at least two additional steps in the production of mixtures of this type.

There is thus a demand for compounds which allow the desired cholesteric pitch to be induced in nematic base mixtures and at the same time allow these mixtures to be stabilised.

It has been found that this requirement can be achieved through the use of corresponding compounds.

Compound of the formula I

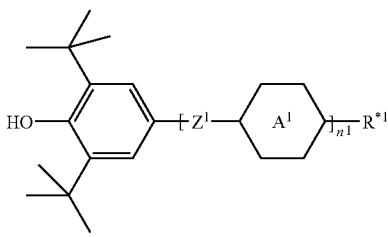

(I)

in which
$R^{*1}$ denotes a chiral radical,
$Z^1$, if present more than once, in each case, independently of one another, denotes —$CH_2$—$CH_2$—, —CH=CH—, —C≡C—, —COO—, —OCO—, —$CH_2$O—, —OCH$_2$—, —CF$_2$O—, —OCF$_2$—, —(CH$_2$)$_4$—, —CF=CF—, —CH=CF—, —CF=CH—, —CH$_2$—, —CF$_2$—, —CHF—, —O—, —S— or a single bond,

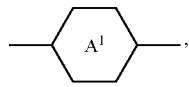

if present more than once, in each case,
independently of one another, denotes
(a) a trans-1,4-cyclohexylene radical, in which, in addition, one or more non-adjacent CH$_2$ groups may be replaced by —O— and/or —S—,
(b) a 1,4-cyclohexenylene radical,
(c) a 1,4-phenylene radical, in which, in addition, one or two CH groups may be replaced by N, or
(d) a radical selected from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl,
where these radicals (a) to (d) and the phenolic benzene ring may optionally be mono- or polysubstituted by F atoms, and
$n^1$ denotes 0, 1, 2 or 3.

have proven particularly suitable.

In the formula I,

if present more than once, in each case, independently of one another, preferably denotes

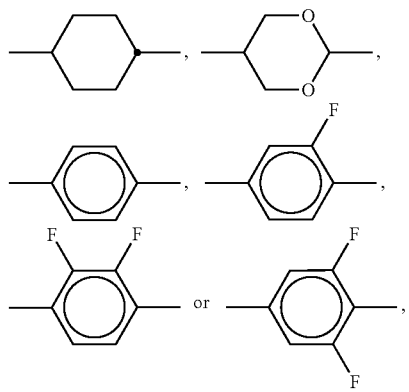

$Z^1$, if present more than once, in each case, independently of one another, preferably denotes —$CH_2$—$CH_2$—, —CH=CH—, —C≡C—, —COO— or a single bond, particularly preferably —$CH_2$—$CH_2$— or a single bond, especially preferably a single bond, and $n^1$ preferably denotes 0, 1 or 2, preferably 0 or 1.

Preference is furthermore given to compounds of the formula Ia

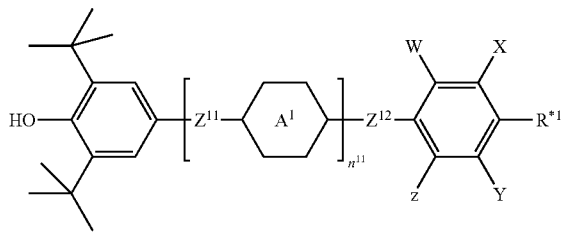

Ia in which
R*¹ and

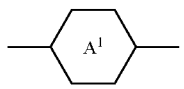

have the meaning given above in the case of the formula I, and
Z¹¹ and Z¹² each, independently of one another, have the meaning given above for Z¹ in the case of the formula I, and
$n^{11}$ denotes 0, 1 or 2, preferably 0 or 1, and
W, X, Y and Z each, independently of one another, denote H, F, Cl, alkyl or alkoxy, preferably having 1 to 7 C atoms.

Preference is furthermore given to compounds of the formula I, preferably of the formula Ia, characterised in that R*¹ denotes a chiral radical of the formula

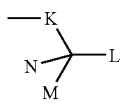

I in which
K denotes a single bond, alkylene having 1 to 9, preferably having 1 to 5 C atoms, alkenylene or alkynylene having 2 to 9, preferably having 2 to 5 C atoms, where one, two or more of the —CH₂— groups present in all three types of group may each be replaced by —O—, —C═O— or —S—, but where no two O atoms are bonded directly to one another and all three types of group may optionally be substituted by halogen, preferably by fluorine, and K preferably denotes a single bond, —CH₂—, —O—, —CO—O—, —CO—O—CH₂—, —O—CO—, —CH₂—CH₂—, —CH═CH— or —C═C—, and
L, M and N, each independently of one another, but differently from one another and from the remainder of the molecule including the group K, denote hydrogen, halogen, preferably F, aryl or cycloalkyl, alkyl or alkoxy having 1 to 11, preferably 1 to 7 C atoms, alkenyl, alkenyloxy, alkynyl or alkynyloxy having 2 to 11, preferably 2 to 7 C atoms, where one, two or more of the —CH₂— groups present in all six types of group may each be replaced by —O—, —C═O— or —S—, but where no two O atoms are bonded directly to one another and all six types of group may optionally be substituted by halogen, preferably by fluorine, and L, M and/or N preferably denote phenyl, alkyl, alkoxy, alkenyl or alkynyl.

In these compounds,
R*¹ denotes in particular a chiral radical selected from the group consisting of the radicals of the formulae

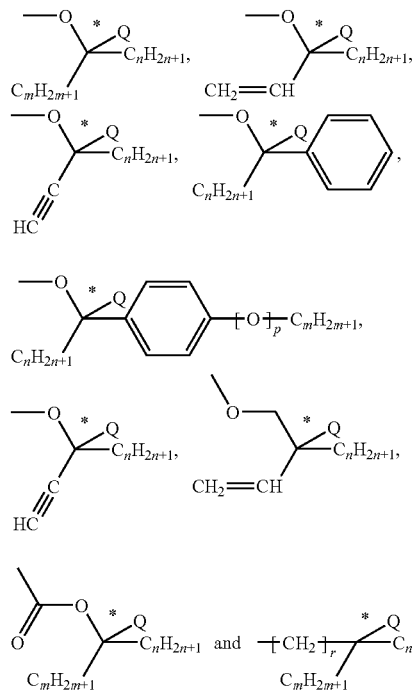

in which
Q denotes H or halogen, preferably H or F, in particular H,
n and m are different from one another and otherwise, independently of one another, denote 1 to 11,
p denotes 0 or 1, and
r denotes 0 to 4, preferably 0 to 2.
Preferably denotes

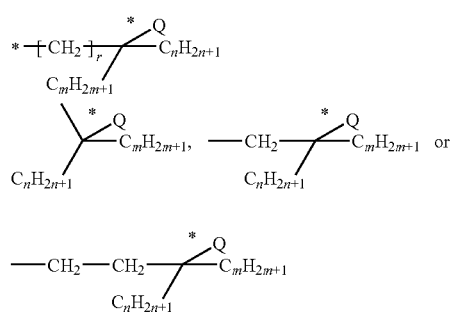

in which the parameters have the meaning given above.
Particular preference is given to compound of the formula Ia selected from the group consisting of the compounds of the formulae Ia-1 to Ia-9

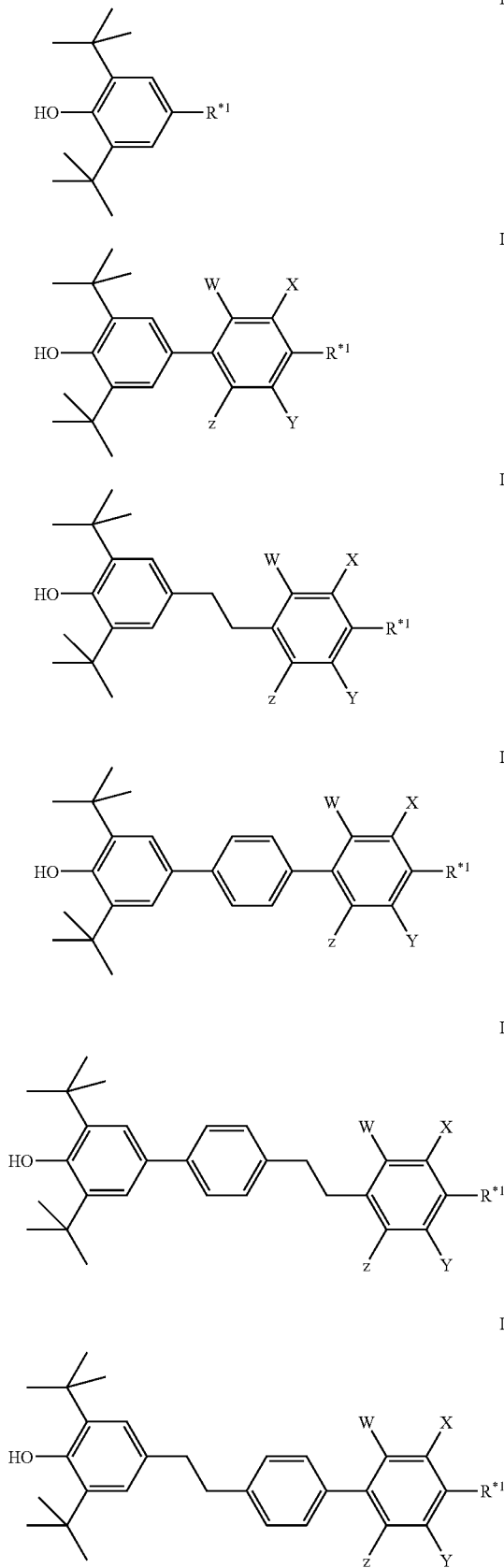
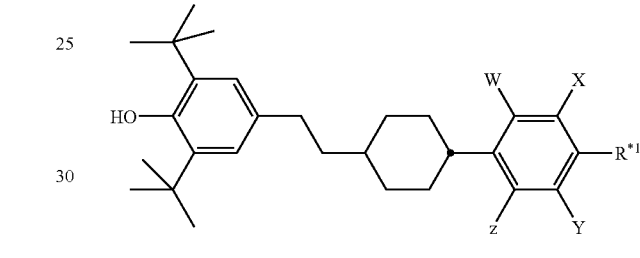
in which the parameters have the meaning given above, and W and Z preferably denote H.
The compounds of the formula I are prepared in accordance with scheme I and II.
Scheme I
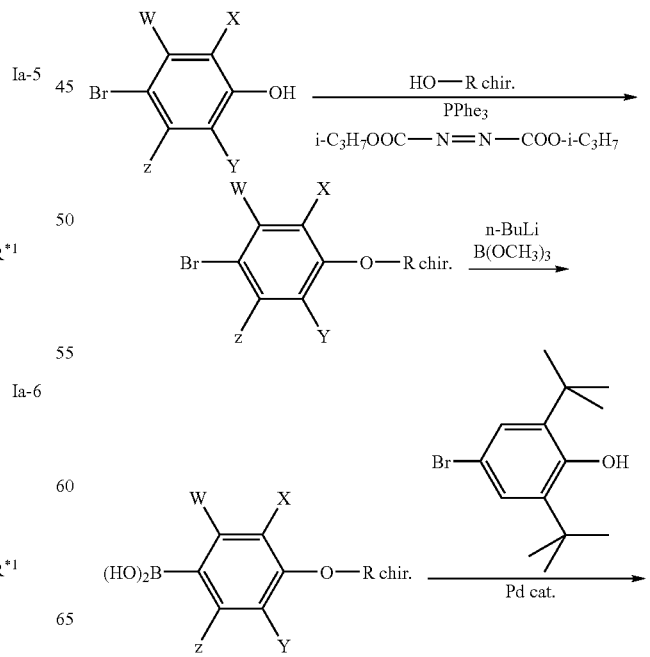

-continued

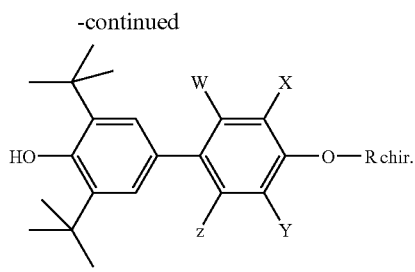

in which "R chir." denotes R*¹, and the parameters have the meaning given above under the formula I.

Scheme II

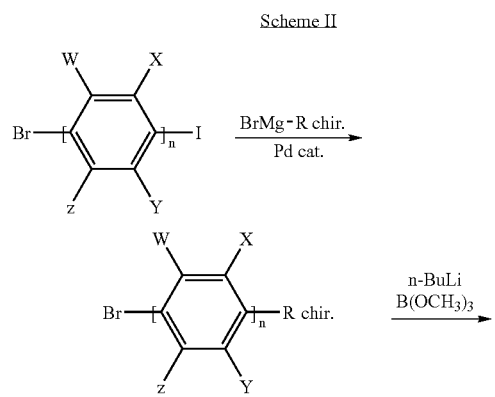

in which "R chir." denotes R*¹, and the parameters have the meaning given above under the formula I.

The liquid-crystal media according to the invention comprise one or more compounds of the formula I.

In a preferred embodiment, the liquid-crystal media in accordance with the present invention comprise a) one or more chiral compounds of the formula I b) one or more dielectrically neutral compounds of the formula II

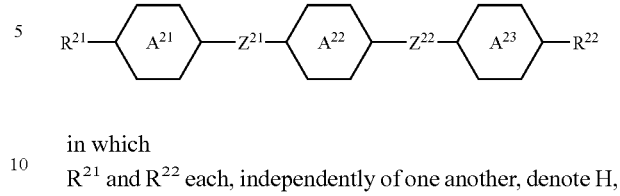

in which $R^{21}$ and $R^{22}$ each, independently of one another, denote H, an alkyl group having 1 to 15 C atoms which is monosubstituted by CN or $CF_3$ or at least monosubstituted by halogen, in which, in addition, one or more $CH_2$ groups may each, independently of one another, be replaced by —O—, —S—, —CH=CH—, —CF=CF—, —CF=CH—, —CH=CF—,

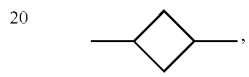

—CO—, —CO—O—, —O—CO— or —O—CO—O— in such a way that O atoms are not linked directly to one another, preferably alkyl and alkoxy having 1 to 12 C atoms, alkoxyalkyl, alkenyl or alkenyloxy having 2 to 12 C atoms, $Z^{21}$ and $Z^{22}$ each, independently of one another, have the meaning given above for $Z^{11}$ in the case of the formula I,

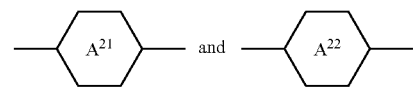

each, independently of one another, denote

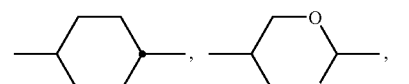
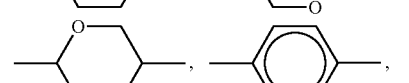
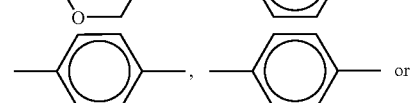

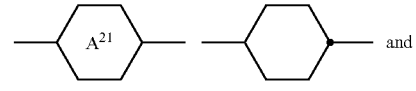

-continued

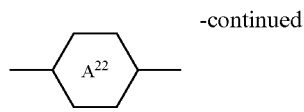

particularly preferably, if present, denote

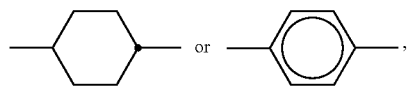

l denotes 0 or 1, and c) one or more dielectrically positive compounds or d) one or more dielectrically negative compounds and optionally e) one or more dielectrically neutral compound(s).

The liquid-crystal media in accordance with the present invention preferably comprise one or more compounds having at least one olefinic double bond and/or containing at least one —$CF_z$—O— group. Preference is given to the compounds which have at least one olefinic double bond, dielectrically positive or dielectrically neutral.

Particular preference is given to dielectrically neutral compounds of the formula II, in which at least one of the following conditions is preferably met:

a) $R^{21}$ denotes alkenyl, b) $R^{22}$ denotes alkenyl and c) at least one of the bridges $Z^{21}$ and $Z^{22}$ present denotes —CH=CH—.

The liquid-crystal media preferably comprise one or more compounds of the formula II which contain no biphenyl unit.

The liquid-crystal media particularly preferably comprise one or more compounds of the formula II in which two adjacent rings are linked directly and preferably denote

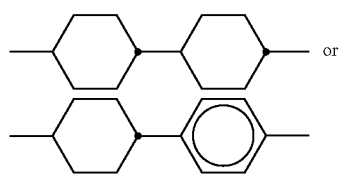

The liquid-crystal medium preferably comprises one or more compounds selected from the group consisting of the compounds of the formulae II1 to II4

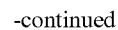

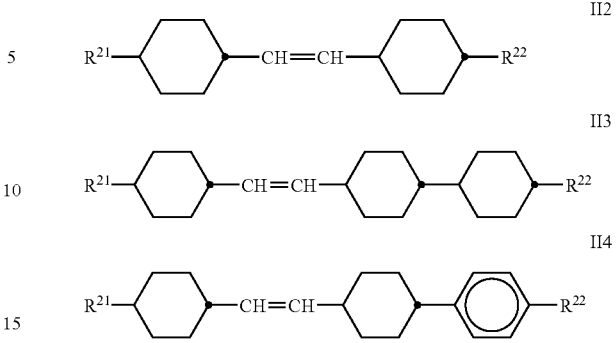

in which $R^{21}$ and $R^{22}$ each have the meaning given above in the case of the formula II, and at least one of the groups $R^{21}$ and $R^{22}$ in the formula II1 preferably denote alkenyl. Preferably, $R^{21}$ is alkyl or alkoxy having 1-5 C atoms and $R^{22}$ is alkenyl.

Here, as throughout the present application, unless expressly stated otherwise, the term compounds, for clarification also written as compound(s), denotes both one compound and a plurality of compounds.

The liquid-crystal medium preferably comprises one or more compounds of the formula III

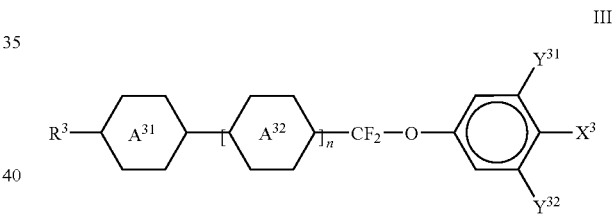

in which $R^3$ denotes alkyl or alkoxy having 1 to 7 C atoms, alkenyl, alkenyloxy or oxaalkyl having 2 to 7 C atoms, preferably alkyl or alkenyl, preferably having 1 to 5 or 2 to 5 C atoms respectively,

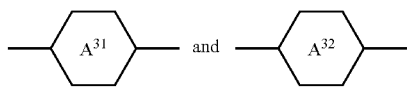

each, independently of one another, denote

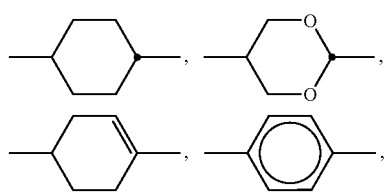

-continued

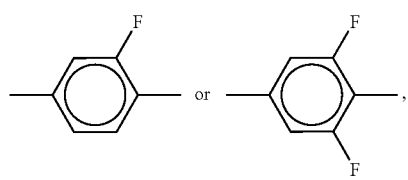

preferably

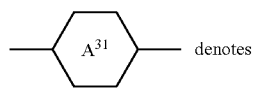 denotes

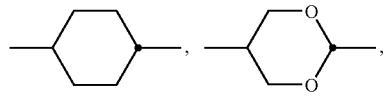,

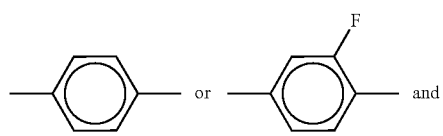 and

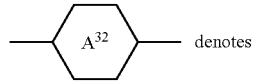 denotes

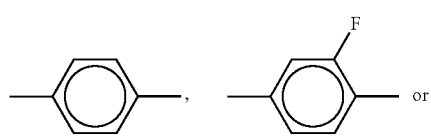 or

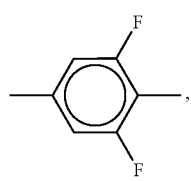, $X^3$ denotes F, Cl, —OCF$_2$H, —OCF$_3$ or —CF$_3$, preferably F, Cl or —CF$_3$, and $Y^{31}$ and $Y^{32}$ each, independently of one another, denote H or F.

The liquid-crystal medium preferably comprises one or more compounds of the formula III selected from the group consisting of the compounds of the formulae III1 to III5, preferably III1, III4 and III5, particularly preferably III1 and III5,

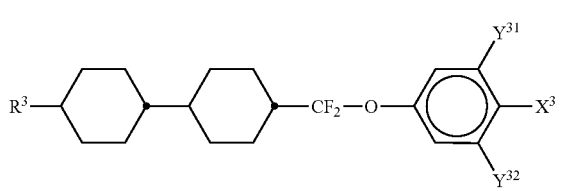

III1

-continued

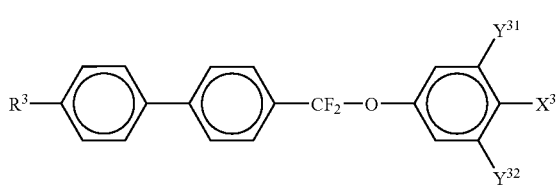

III2

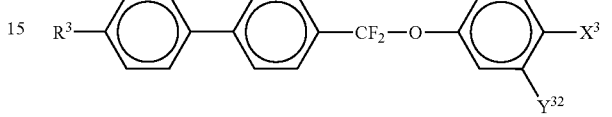

III3

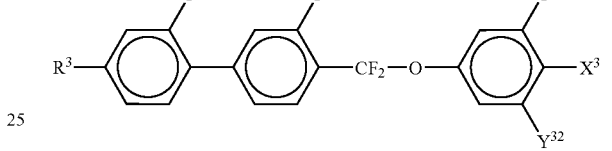

III4

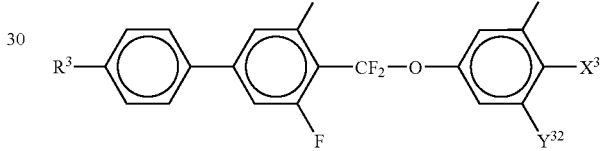

III5

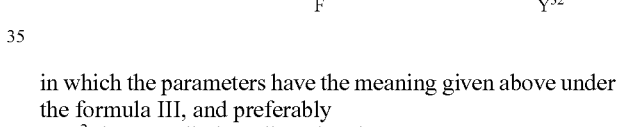

in which the parameters have the meaning given above under the formula III, and preferably R$^3$ denotes alkyl or alkenyl and X$^3$ and Y$^{31}$ both denote F and Y$^{32}$ denotes H or F, preferably F, or X$^3$ denotes —OCF$_3$ and Y$^{31}$ denotes F and Y$^{32}$ denotes H or F, preferably H.

In the case of the nematic or nematogenic compounds, in particular in the case of the compounds of the formulae II and III, the individual compounds are generally employed in concentrations of 1% to 30%, preferably 2% to 20% and particularly preferably 4% to 16%.

In a particularly preferred embodiment, which may be identical and preferably is identical with the above-described preferred embodiments for the preferred concentration ranges, the liquid-crystal media comprise one or more compounds of the formula Ia and one or more compounds of the formula II, preferably selected from the group consisting of the compounds of the formulae II2 to II4, and/or one or more compounds of the formula III, preferably selected selected from the group consisting of the compounds of the formulae III1 and III5.

The liquid-crystal media according to the invention preferably each have nematic phases at least from −10° C. to 70° C., preferably from −30° C. to 80° C. and very particularly preferably from −40° C. to 90° C. The term "have a nematic phase" here means firstly that no smectic phase and no crystallisation is observed at low temperatures at the corresponding temperature and secondly also that no clearing occurs on heating from the nematic phase. The investigation at low temperatures is carried out in a flow viscometer at the corresponding temperature and checked by storage in test cells having a layer thickness corresponding to the electro-optical application for at least 100 hours. At high temperatures, the clearing point is measured in capillaries by conventional methods.

In addition, the liquid-crystal media according to the invention have relatively small values for the Freedericksz threshold voltage of less than or equal to 3.0 V, preferably less than or equal to 2.0 V, particularly preferably less than or equal to 1.5 V and very particularly preferably less than or equal to 1.0 V.

These preferred values for the individual physical properties are also observed in each case combined with one another. Thus, media according to the invention have, in particular, the following property combinations:

The term "alkyl" preferably covers straight-chain and branched alkyl groups having 1-7 carbon atoms, in particular the straight-chain groups methyl, ethyl, propyl, butyl, pentyl, hexyl and heptyl. Groups having 2-5 carbon atoms are generally preferred.

The term "alkenyl" preferably covers straight-chain and branched alkenyl groups having 2-7 carbon atoms, in particular the straight-chain groups. Particularly preferred alkenyl groups are $C_2$-$C_7$-1 E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1 E-alkenyl, $C_4$-$C_7$-3E-alkenyl and $C_5$-$C_7$-4-alkenyl. Examples of further preferred alkenyl groups are vinyl, 1 E-propenyl, 1 E-butenyl, 1 E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" or "alkoxyalkyl" preferably covers straight-chain radicals of the formula $C_nH_{2n+1}$—O—$(CH_2)_m$, in which n and m each, independently of one another, denote 1 to 6. n is preferably=1 and m is preferably 1 to 6.

In the present application, the term dielectrically positive compounds means compounds having a $\Delta\epsilon > 1.5$, dielectrically neutral compounds means those in which $-1.5 \leq \Delta\epsilon \leq 1.5$, and dielectrically negative compounds means those having a $\Delta\epsilon < -1.5$. The dielectric anisotropy of the compounds is determined here by dissolving 10% of the compounds in a liquid-crystalline host and determining the capacitance of this mixture at 1 kHz in at least one test cell having a density of 10 µm with a homeotropic surface alignment and in at least one test cell having a density of 10 µm with a homogeneous surface alignment. The measurement voltage is typically 0.5 V to 1.0 V, but is always less than the capacitive threshold of the respective liquid-crystal mixture.

The host mixture used for dielectrically positive compounds is ZLI-4792 and the host mixture used for dielectrically neutral and dielectrically negative compounds is ZLI-3086, both from Merck KGaA, Germany. The change in the dielectric susceptibilities of the host mixture after addition of the compound to be investigated and extrapolation to 100% of the compound employed gives the values for the respective compounds to be investigated.

The term threshold voltage usually relates to the optical threshold for 10% relative contrast ($V_{10}$).

In relation to the liquid-crystal mixtures of negative dielectric anisotropy, however, the term threshold voltage in the present application is used for the capacitive threshold voltage ($V_0$), also known as the Freedericksz threshold, unless explicitly stated otherwise.

All concentrations in this application, unless explicitly stated otherwise, are given in percent by weight and relate to the corresponding mixture as a whole. All physical properties are and have been determined in accordance with "Merck Liquid Crystals, Physical Properties of Liquid Crystals", status Nov. 1997, Merck KGaA, Germany, and apply to a temperature of 20° C., unless explicitly stated otherwise. $\Delta n$ is determined at 589 nm and $\Delta\epsilon$ at 1 kHz. The threshold voltages and the other electro-optical properties were determined in test cells produced at Merck KGaA, Germany, using white light by means of a commercial measuring instrument from Otsuka, Japan. To this end, cells were selected having, depending on the $\Delta n$ of the liquid crystals, a thickness corresponding to an optical retardation d·$\Delta n$ of the cells of about 0.50 µm. The cells were operated in so-called "normally white mode" with polarisers parallel to the rubbing directions on the adjacent substrates. The characteristic voltages were all determined with perpendicular viewing. The threshold voltage has been indicated as $V_{10}$ for 10% relative contrast, the mid-grey voltage $V_{50}$ for 50% relative contrast and the saturation voltage $V_{90}$ for 90% relative contrast.

In the case of the liquid-crystal media of negative dielectric anisotropy, the threshold voltage was determined as the capacitive threshold $V_0$ (also known as the Freedericksz threshold) in cells with a liquid-crystal layer aligned homeotropically by means of lecithin.

The liquid-crystal media according to the invention may, if necessary, also comprise further additives and optionally also further chiral dopants in the conventional amounts. The amount of these additives employed is in total 0% to 10%, based on the amount of the mixture as a whole, preferably 0.1% to 6%. The concentration of the individual compounds employed is preferably 0.1 to 3%. The concentration of these and similar additives is not taken into account when indicating the concentrations and the concentration ranges of the liquid-crystal compounds in the liquid-crystal media.

The compositions consist of a plurality of compounds, preferably 3 to 30, particularly preferably 6 to 20 and very particularly preferably 10 to 16 compounds, which are mixed in a conventional manner. In general, the desired amount of the components used in lesser amount is dissolved in the components making up the principal constituent, advantageously at elevated temperature. If the selected temperature is above the clearing point of the principal constituent, the completion of the dissolution process is particularly easy to observe. However, it is also possible to prepare the liquid-crystal mixtures in other conventional ways, for example using premixes or from a so-called "multibottle system".

By means of suitable additives, the liquid-crystal phases according to the invention can be modified in such a way that they can be employed in any type of LCD that has been disclosed hitherto and in particular in ECB displays, VA displays, PA LCDs, ASM LCDs and IPS displays.

The examples below serve to illustrate the invention without restricting it. In the examples, the melting point T (C,N), the transition from the smectic (S) phase to the nematic (N) phase T(S,N) and the clearing point T (N,I) of a liquid-crystal substance are indicated in degrees Celsius. The percentages above and below are, unless explicitly stated otherwise, percent by weight, and the physical properties are the values at 20° C., unless explicitly stated otherwise.

All the indicated values for temperatures in this application are ° C. and all temperature differences are correspondingly differential degrees, unless explicitly stated otherwise.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m C atoms respectively. The coding in Table B is self-evident. In Table A, only the acronym for the parent structure is indicated. In individual cases, the acronym for the parent structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nN.F.F | $C_nH_{2n+1}$ | CN | F | F |
| nF | $C_nH_{2n+1}$ | F | H | H |

-continued

| Code for $R^1$, $R^2$, $L^1$, $L^2$ | $R^1$ | $R^2$ | $L^1$ | $L^2$ |
|---|---|---|---|---|
| nOF | $OC_nH_{2n+1}$ | F | H | H |
| nF.F | $C_nH_{2n+1}$ | F | H | F |
| nF.F.F | $C_nH_{2n+1}$ | F | F | F |
| nmF | $C_nH_{2n+1}$ | $C_mH_{2m+1}$ | F | H |
| nCF$_3$ | $C_nH_{2n+1}$ | CF$_3$ | H | H |
| nOCF$_3$ | $C_nH_{2n+1}$ | OCF$_3$ | H | H |
| nOCF$_3$.F | $C_nH_{2n+1}$ | OCF$_3$ | H | F |
| nOCF$_3$.F.F | $C_nH_{2n+1}$ | OCF$_3$ | F | F |
| nOCF$_2$.F | $C_nH_{2n+1}$ | OCHF$_2$ | H | H |
| nOCF$_2$.F | $C_nH_{2n+1}$ | OCHF$_2$ | H | F |
| nOCF$_2$.F.F | $C_nH_{2n+1}$ | OCHF$_2$ | F | F |
| nS | $C_nH_{2n+1}$ | NCS | H | H |
| rVsN | $C_rH_{2r+1}$—CH=CH—$C_sH_{2s}$— | CN | H | H |
| nEsN | $C_rH_{2r+1}$—O—$C_sH_{2s}$— | CN | H | H |
| nAm | $C_nH_{2n+1}$ | COOC$_m$H$_{2m+1}$ | H | H |
| nCl | $C_nH_{2n+1}$ | Cl | H | H |
| nCl.F | $C_nH_{2n+1}$ | Cl | H | F |
| nCl.F.F | $C_nH_{2n+1}$ | Cl | F | F |

TABLE A

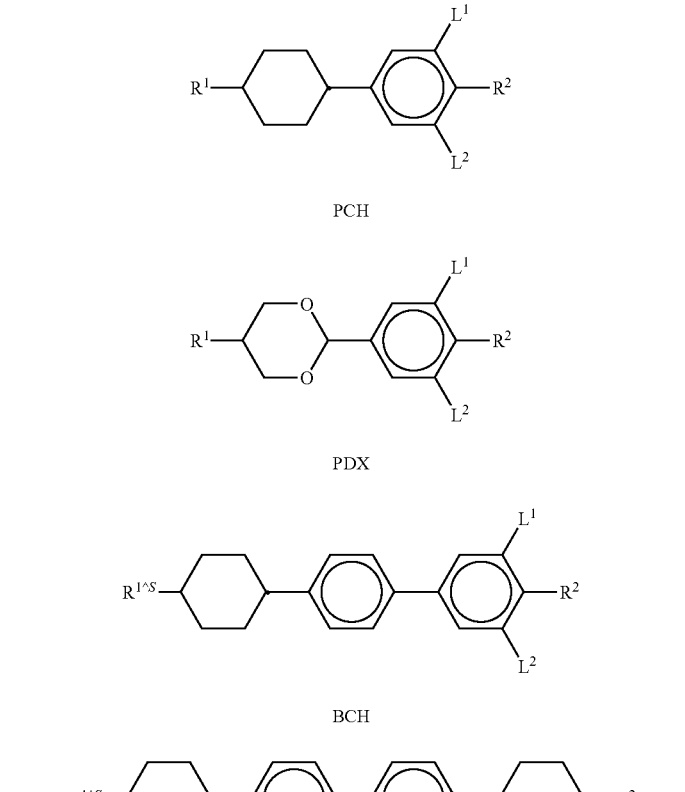

PCH

PDX

BCH

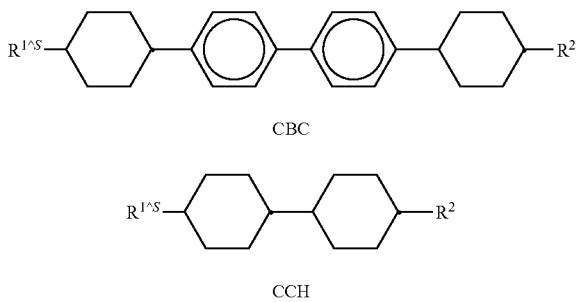

CBC

CCH

TABLE A-continued
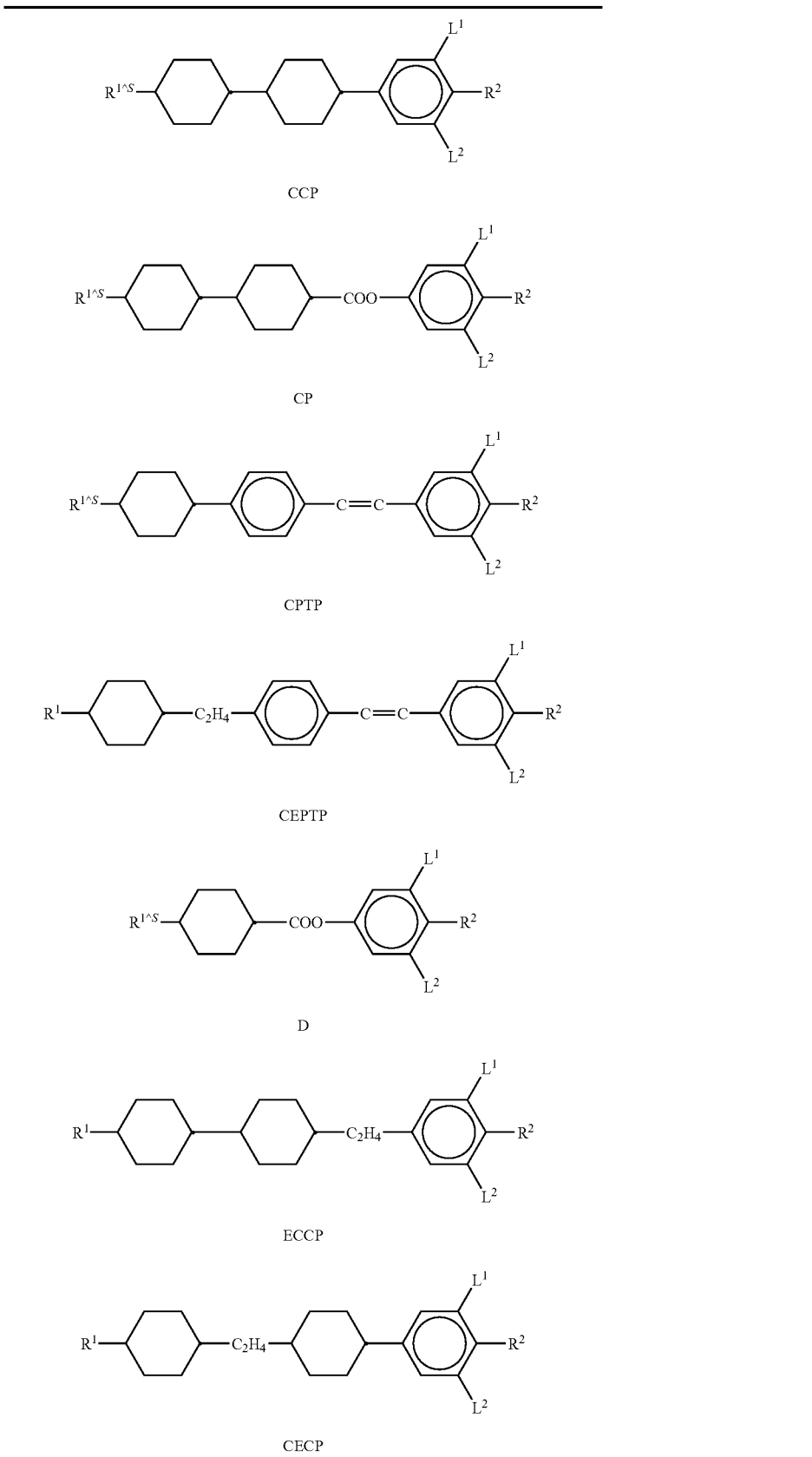

TABLE A-continued
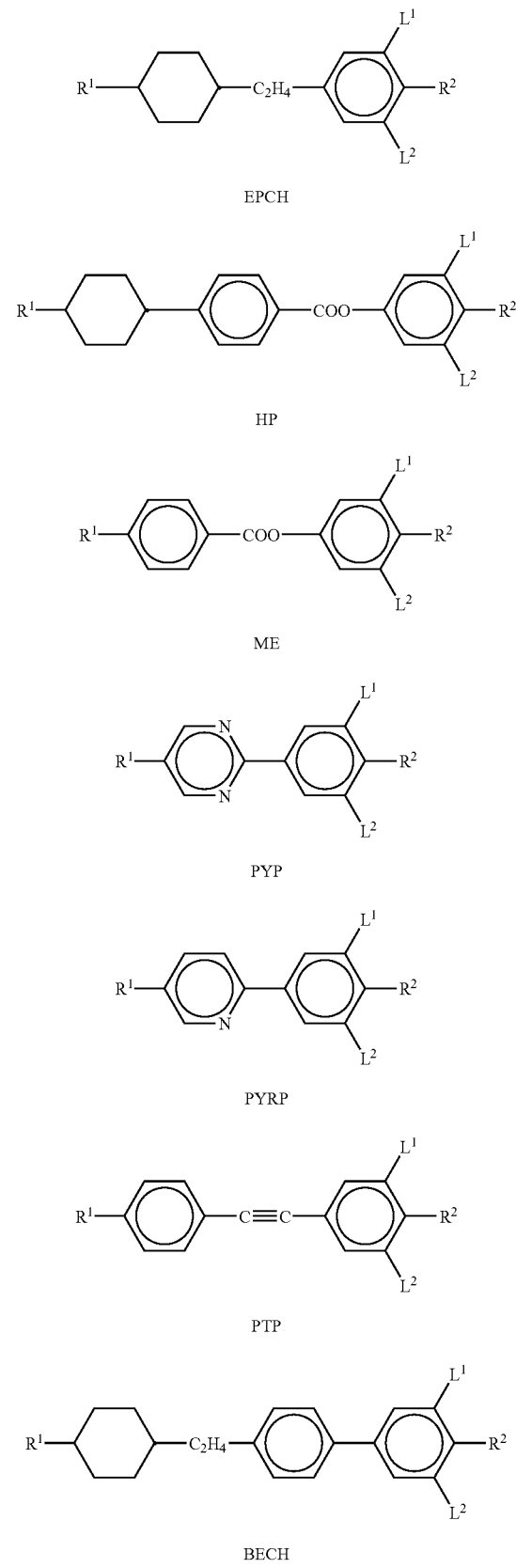

TABLE A-continued
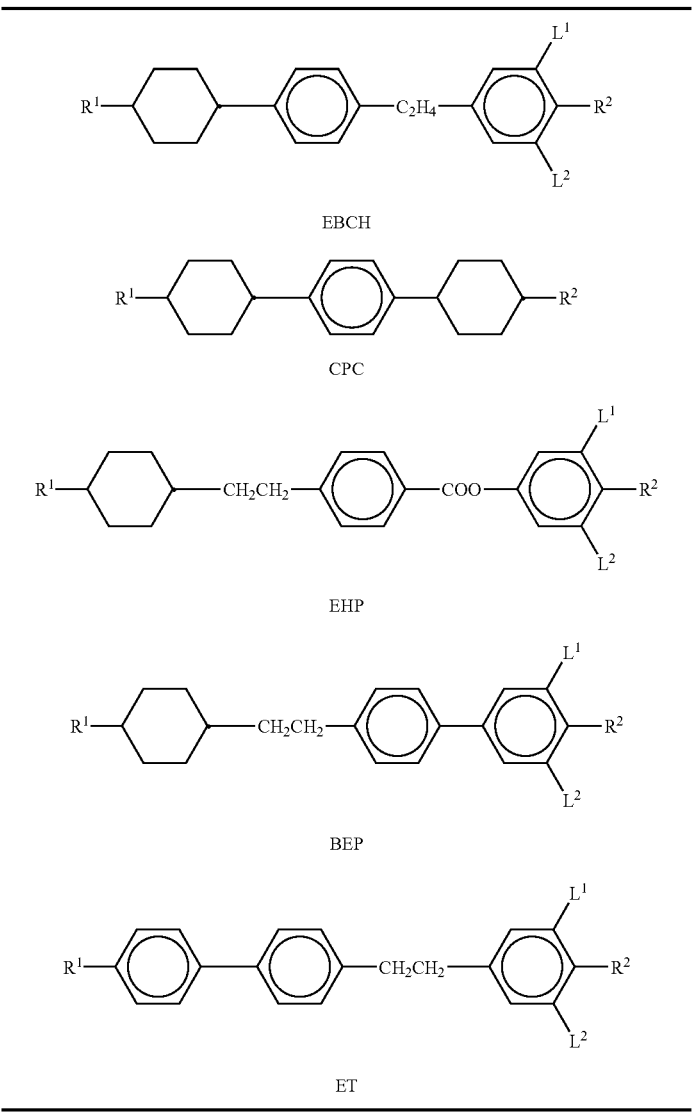
EBCH
CPC
EHP
BEP
ET
TABLE B
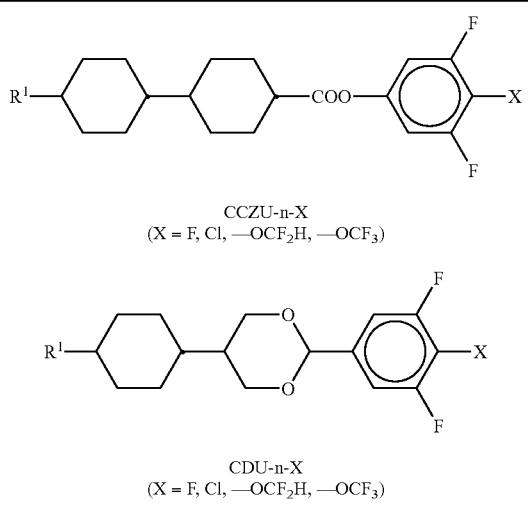
CCZU-n-X
(X = F, Cl, —OCF$_2$H, —OCF$_3$)
CDU-n-X
(X = F, Cl, —OCF$_2$H, —OCF$_3$)

TABLE B-continued
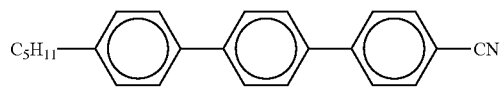
T15
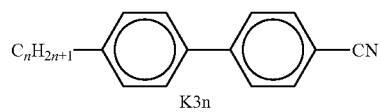
K3n
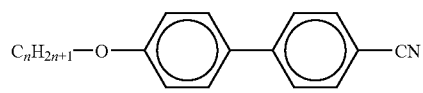
M3n
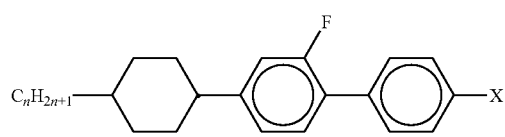
CGP-n-X
(X = F, Cl, —OCF$_2$H, —OCH$_3$)
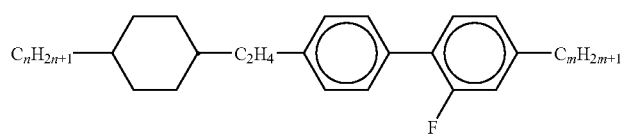
Inm
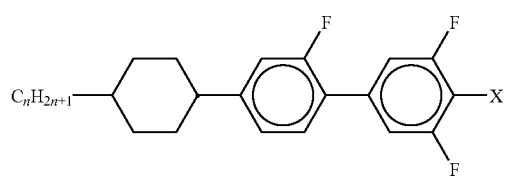
CGU-n-X
(X = F, Cl, —OCF$_2$H, —OCF$_3$)
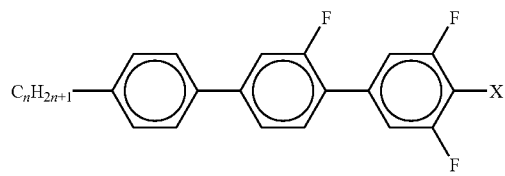
PGU-n-X
(X = F, Cl, —OCF$_2$H, —OCF$_3$)
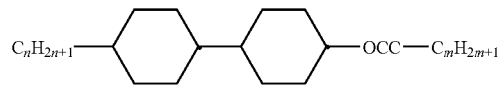
C-nm
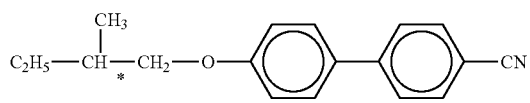
C15

TABLE B-continued
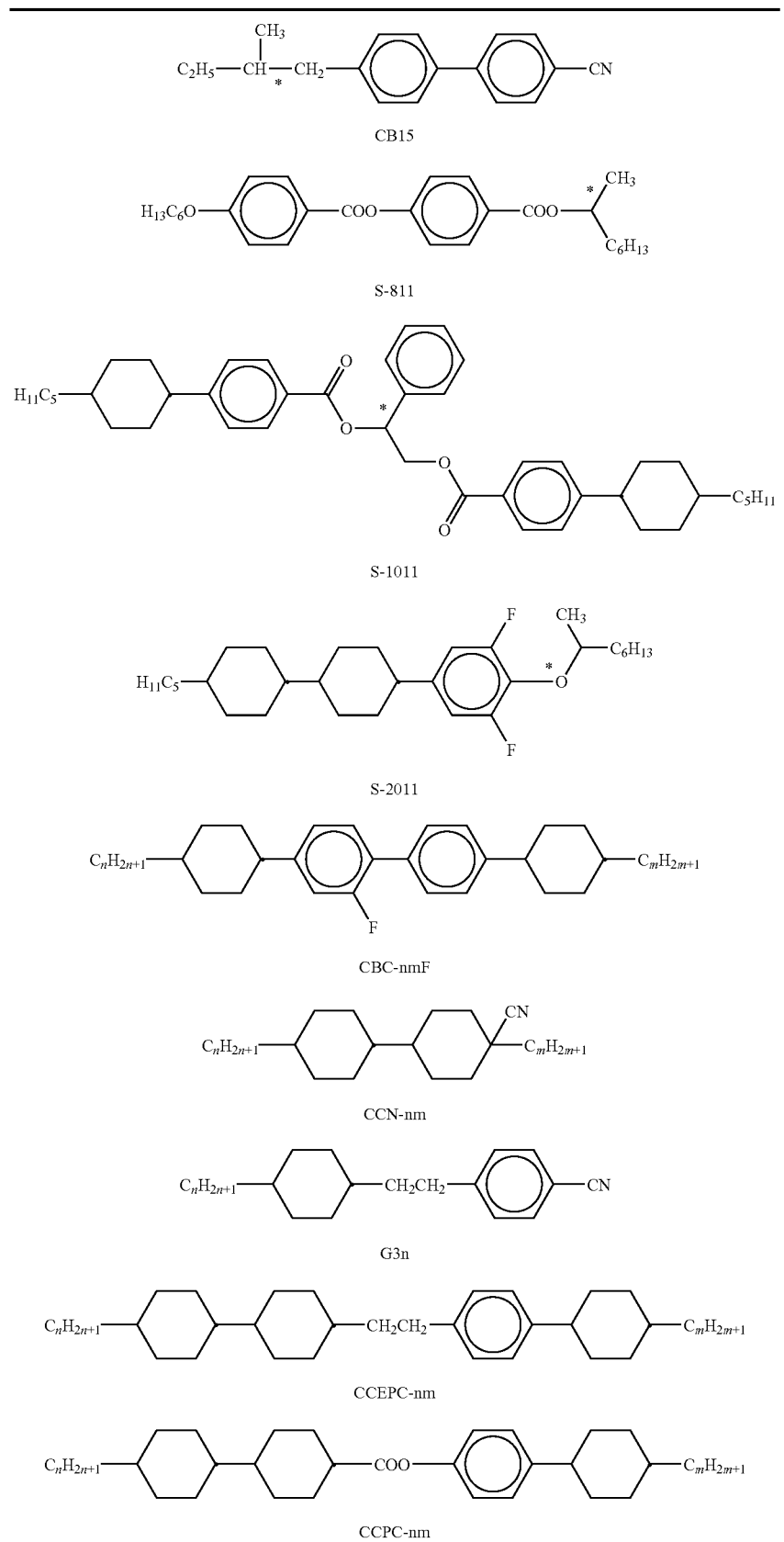

TABLE B-continued
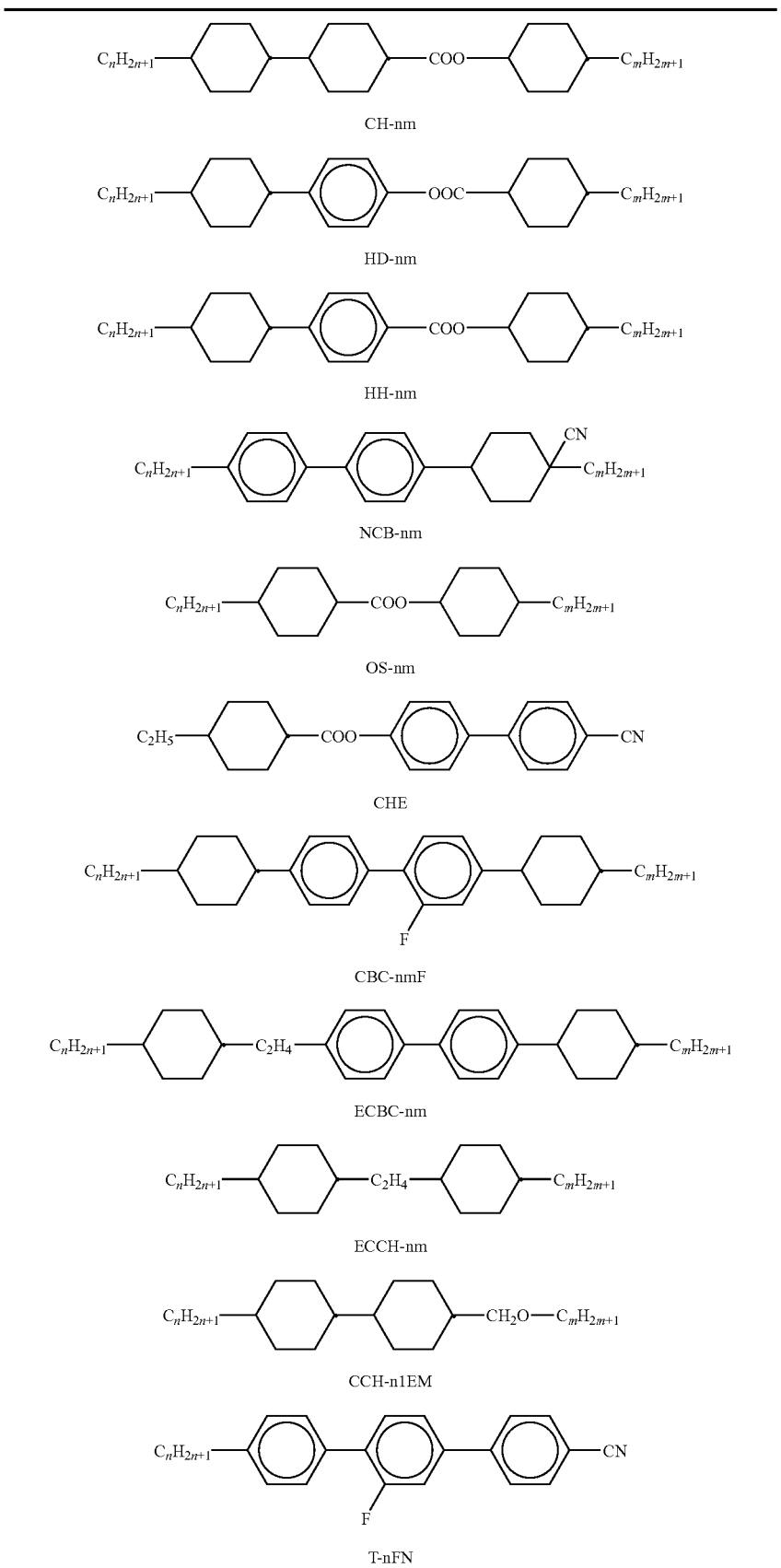

TABLE B-continued
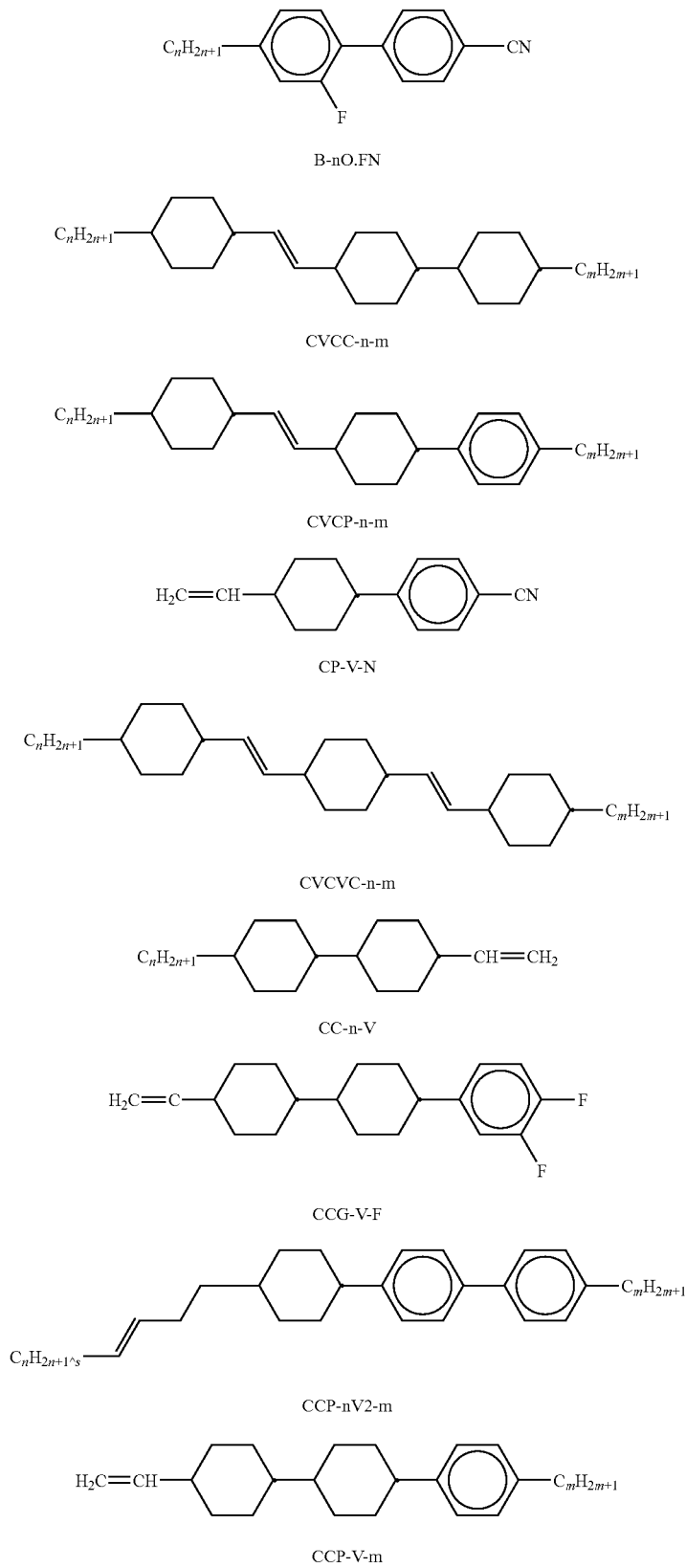

TABLE B-continued
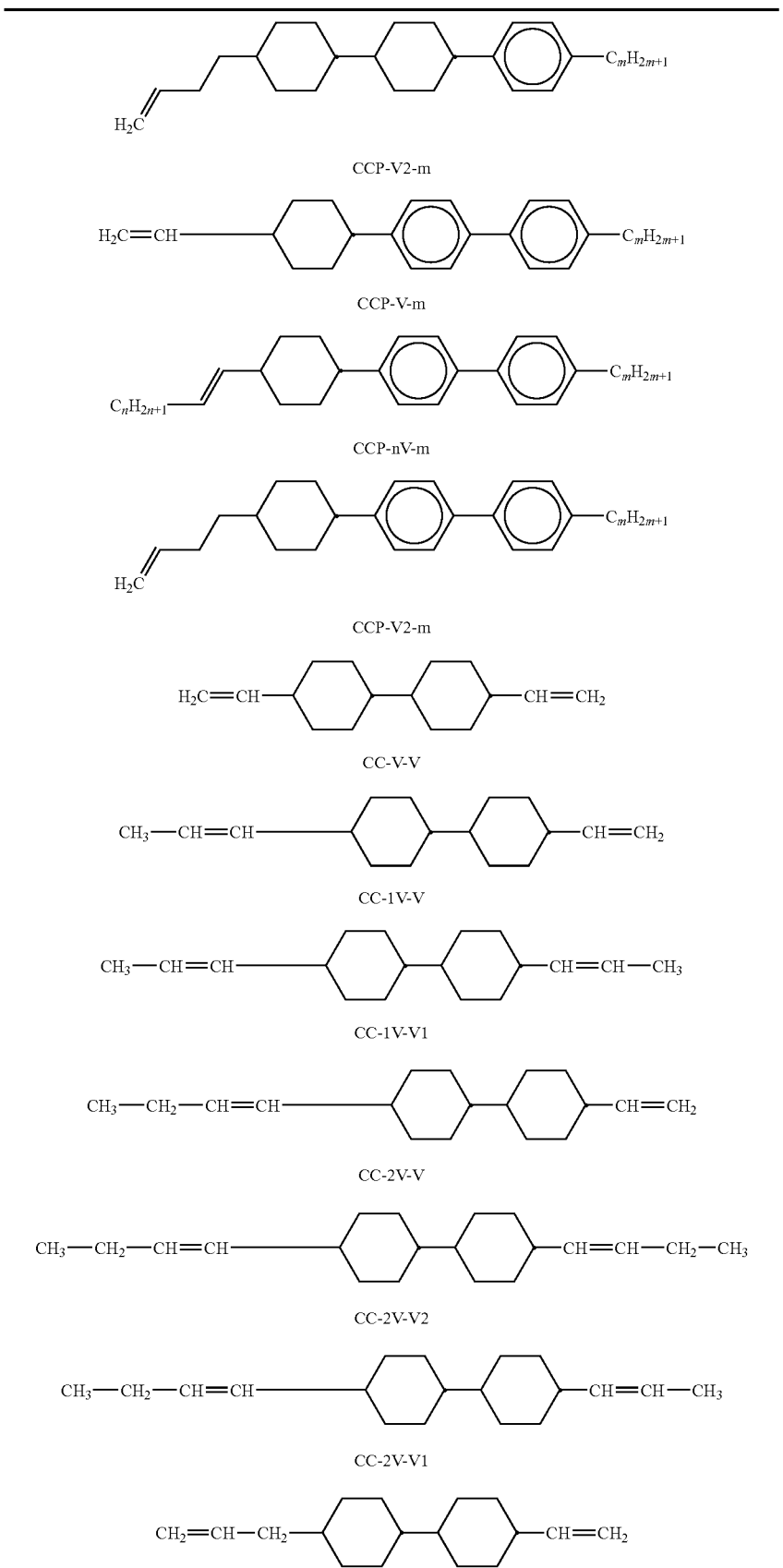

TABLE B-continued
CC-V1-V
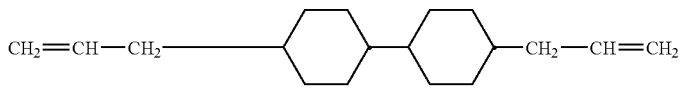
CC-V1-1V
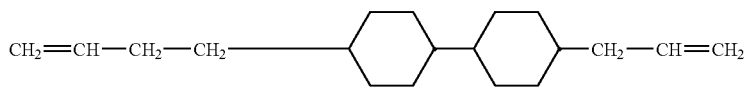
CC-V2-1V
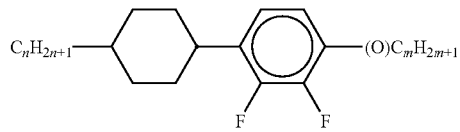
PCH-n(O)mFF
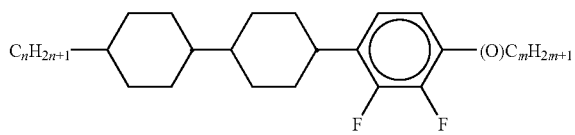
CCP-n(O)mFF
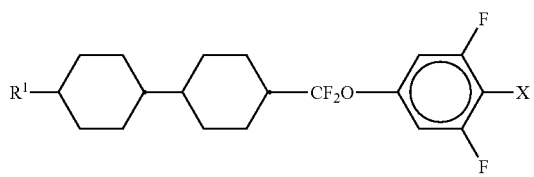
CCQU-n-X
(X = F, Cl, —OCF$_2$H, —OCH$_3$)
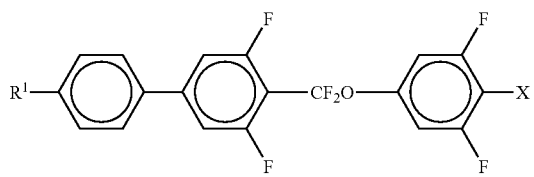
PUQU-n-X
(X = F, Cl, —OCF$_2$H, —OCH$_3$)

EXAMPLES

The following examples are intended to explain the invention without limiting it. Above and below, percentages are percent by weight. All temperatures are given in degrees Celsius. An denotes the optical anisotropy (589 nm, 20° C.), Δ∈ the dielectric anisotropy (1 kHz, 20° C.), H.R. the voltage holding ratio (at 100° C., after 5 minutes in the oven, 1 V), and $V_{10}$, $V_{50}$ and $V_{90}$ the threshold voltage, mid-grey voltage and saturation voltage respectively, and the capacitive threshold voltage $V_0$ were determined at 20° C.

Substance Examples

Example 1

Preparation of Chiral 3,5-di-tert-butyl-3',5'-difluoro-4'-(1-methylheptyloxy)biphenyl-4-ol Step 1: Preparation of 3,5-difluoro-4-(1-methylheptyloxy)bromobenzene

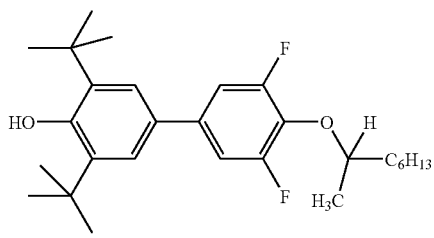

12.0 g of 4-bromo-2,6-difluorophenol, 10.0 ml of (S)-(+)-2-octanol and 16.5 g of triphenylphosphine were dissolved in 300 ml of tetrahydrofuran at about 20° C. with stirring under a nitrogen atmosphere. 12.5 ml of anhydrous (max. 0.0075% of H₂O) diisopropyl azodicarboxylate were subsequently added dropwise. The reaction proceeds exothermically. The rate of addition was selected in such a way that the temperature of the mixture did not exceed 45° C. The reaction solution was subsequently stirred for 2 h, and the solvent was then removed in a rotary evaporator. The crude product was purified in a mixture of chlorobutane and heptane in the ratio 1:1 over 2 l of silica gel, giving 14.5 g of 3,5-difluoro-4-(1-methylheptyloxy)bromobenzene as a clear liquid.

Step 2: Preparation of 3,5-difluoro-4-(1-methylheptyloxy)phenylboronic acid 14.5 g of 1-bromo-3,5-difluoro-4-(1-methylheptyloxy)benzene from step 1 were dissolved in 150 ml of diethyl ether and cooled to −70° C. At this temperature, with cooling, firstly 31.0 ml of a 15% solution of butyllithium in n-hexane were slowly added dropwise, the mixture was stirred at the same temperature for 1 h, and then 5.6 ml of trimethyl borate were slowly added dropwise, and the mixture was stirred for a further h. The temperature of the reaction solution was slowly allowed to rise to −10° C. The mixture was then hydrolysed with distilled water, and the pH was adjusted to 2 using hydrochloric acid. The organic phase was separated off, and the aqueous phase was extracted with MTB ether. The product was subjected to conventional purification and dried over Na₂SO₄, giving 13.9 g of 3,5-difluoro-4-(1-methylheptyloxy)phenylboronic acid.

Step 3: Preparation of 3,5-di-tert-butyl-3',5'-difluoro-4'-(1-methylheptyloxy)biphenyl-4-ol 3,5-Difluoro-4-(1-methylheptyloxy)phenylboronic acid from step 2 were dissolved in 100 ml of 2-propanol with 12.0 g of 2,6-di-tert-butyl-4-bromophenol, 30 mg of palladium(II) acetate and 100 mg of triphenylphosphine, and 30 ml of 2 molar aqueous sodium carbonate solution and 20 ml of distilled water were added. The mixture was then refluxed at 80° C. for 15 h. The reaction mixture was then cooled to about 20° C. and diluted with water. MBT ether was added, and the organic phase was separated off. The product was subjected to conventional purification.

8.4 g of 3,5-di-tert-butyl-3',5'-difluoro-4'-(1-methylheptyloxy)biphenyl-4-ol were obtained as a colourless oil having a glass transition temperature of −21° C.

Examples 2 to 54

The following are prepared analogously to Example 1:

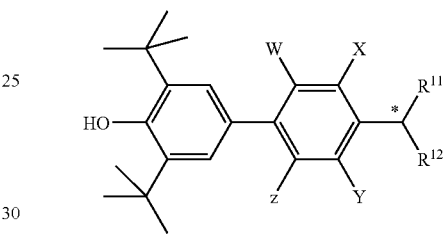

where W and Z denote H.

| No. | Config.§ | $R^{11}$ | $R^{12}$ | X | Y | Properties |
|---|---|---|---|---|---|---|
| 2 | S | $C_2H_5$ | $CH_3$ | H | H | |
| 3 | S | $n\text{-}C_3H_7$ | $CH_3$ | H | H | |
| 4 | S | $n\text{-}C_4H_9$ | $CH_3$ | H | H | |
| 5 | S | $n\text{-}C_5H_{11}$ | $CH_3$ | H | H | |
| 6 | S | $n\text{-}C_6H_{13}$ | $CH_3$ | H | H | |
| 7 | S | $n\text{-}C_3H_7$ | $C_2H_5$ | H | H | |
| 8 | S | $n\text{-}C_4H_9$ | $C_2H_5$ | H | H | |
| 9 | S | $n\text{-}C_5H_{11}$ | $C_2H_5$ | H | H | |
| 10 | S | $n\text{-}C_6H_{13}$ | $C_2H_5$ | H | H | |
| 11 | S | $C_2H_5$ | $CH_3$ | F | H | |
| 12 | S | $n\text{-}C_3H_7$ | $CH_3$ | F | H | |
| 13 | S | $n\text{-}C_4H_9$ | $CH_3$ | F | H | |
| 14 | S | $n\text{-}C_5H_{11}$ | $CH_3$ | F | H | |
| 15 | S | $n\text{-}C_6H_{13}$ | $CH_3$ | F | H | |
| 16 | S | $n\text{-}C_3H_7$ | $C_2H_5$ | F | H | |
| 17 | S | $n\text{-}C_4H_9$ | $C_2H_5$ | F | H | |
| 18 | S | $n\text{-}C_5H_{11}$ | $C_2H_5$ | F | H | |
| 19 | S | $n\text{-}C_6H_{13}$ | $C_2H_5$ | F | H | |
| 20 | S | $C_2H_5$ | $CH_3$ | F | F | |
| 21 | S | $n\text{-}C_3H_7$ | $CH_3$ | F | F | |
| 22 | S | $n\text{-}C_4H_9$ | $CH_3$ | F | F | |
| 23 | S | $n\text{-}C_5H_{11}$ | $CH_3$ | F | F | |

Note:
§Configuration of the alcohol employed.

| No. | Config.§ | $R^{11}$ | $R^{12}$ | X | Y |
|---|---|---|---|---|---|
| 1 | S | $n\text{-}C_6H_{13}$ | $CH_3$ | F | F |
| 24 | S | $n\text{-}C_3H_7$ | $C_2H_5$ | F | F |
| 25 | S | $n\text{-}C_4H_9$ | $C_2H_5$ | F | F |
| 26 | S | $n\text{-}C_5H_{11}$ | $C_2H_5$ | F | F |

-continued

| No. | Config.§ | R¹¹ | R¹² | X | Y |
|---|---|---|---|---|---|
| 27 | S | n-C₆H₁₃ | C₂H₅ | F | F |
| 28 | R | C₂H₅ | CH₃ | H | H |
| 29 | R | n-C₃H₇ | CH₃ | H | H |
| 30 | R | n-C₄H₉ | CH₃ | H | H |
| 31 | R | n-C₅H₁₁ | CH₃ | H | H |
| 32 | R | n-C₆H₁₃ | CH₃ | H | H |
| 33 | R | n-C₃H₇ | C₂H₅ | H | H |
| 34 | R | n-C₄H₉ | C₂H₅ | H | H |
| 35 | R | n-C₅H₁₁ | C₂H₅ | H | H |
| 36 | R | n-C₆H₁₃ | C₂H₅ | H | H |
| 37 | R | C₂H₅ | CH₃ | F | H |
| 38 | R | n-C₃H₇ | CH₃ | F | H |
| 39 | R | n-C₄H₉ | CH₃ | F | H |
| 40 | R | n-C₅H₁₁ | CH₃ | F | H |
| 41 | R | n-C₆H₁₃ | CH₃ | F | H |
| 42 | R | n-C₃H₇ | C₂H₅ | F | H |
| 43 | R | n-C₄H₉ | C₂H₅ | F | H |
| 44 | R | n-C₅H₁₁ | C₂H₅ | F | H |
| 45 | R | n-C₆H₁₃ | C₂H₅ | F | H |
| 46 | R | C₂H₅ | CH₃ | F | F |
| 47 | R | n-C₃H₇ | CH₃ | F | F |
| 48 | R | n-C₄H₉ | CH₃ | F | F |
| 49 | R | n-C₅H₁₁ | CH₃ | F | F |
| 50 | R | n-C₆H₁₃ | CH₃ | F | F |
| 51 | R | n-C₃H₇ | C₂H₅ | F | F |
| 52 | R | n-C₄H₉ | C₂H₅ | F | F |
| 53 | R | n-C₅H₁₁ | C₂H₅ | F | F |
| 54 | R | n-C₆H₁₃ | C₂H₅ | F | F |

Note:
§Configuration of the alcohol employed.

Examples 55 to 72

The following are prepared analogously to Example 1:

| No. | Config.§ | R¹¹ | R¹² |
|---|---|---|---|
| 55 | S | C₂H₅ | CH₃ |
| 56 | S | n-C₃H₇ | CH₃ |
| 57 | S | n-C₄H₉ | CH₃ |
| 58 | S | n-C₅H₁₁ | CH₃ |
| 59 | S | n-C₆H₁₃ | CH₃ |
| 60 | S | n-C₃H₇ | C₂H₅ |
| 61 | S | n-C₄H₉ | C₂H₅ |
| 62 | S | n-C₅H₁₁ | C₂H₅ |
| 63 | S | n-C₆H₁₃ | C₂H₅ |
| 64 | R | C₂H₅ | CH₃ |
| 65 | R | n-C₃H₇ | CH₃ |
| 66 | R | n-C₄H₉ | CH₃ |
| 67 | R | n-C₅H₁₁ | CH₃ |
| 68 | R | n-C₆H₁₃ | CH₃ |
| 69 | R | n-C₃H₇ | C₂H₅ |
| 70 | R | n-C₄H₉ | C₂H₅ |
| 71 | R | n-C₅H₁₁ | C₂H₅ |
| 72 | R | n-C₆H₁₃ | C₂H₅ |

Note:
§Configuration of the alcohol employed.

Examples 73 to 126

The following are prepared analogously to Example 1:

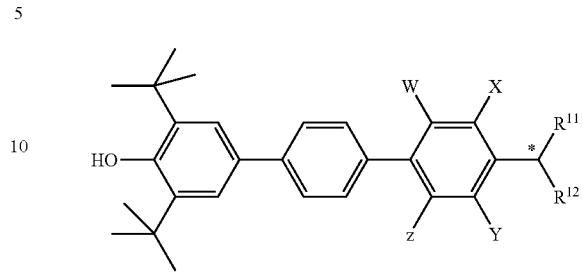

where W and Z denote H.

| No. | Config.§ | R¹¹ | R¹² | X | Y |
|---|---|---|---|---|---|
| 73 | S | C₂H₅ | CH₃ | H | H |
| 74 | S | n-C₃H₇ | CH₃ | H | H |
| 75 | S | n-C₄H₉ | CH₃ | H | H |
| 76 | S | n-C₅H₁₁ | CH₃ | H | H |
| 77 | S | n-C₆H₁₃ | CH₃ | H | H |
| 78 | S | n-C₃H₇ | C₂H₅ | H | H |
| 79 | S | n-C₄H₉ | C₂H₅ | H | H |
| 80 | S | n-C₅H₁₁ | C₂H₅ | H | H |
| 81 | S | n-C₆H₁₃ | C₂H₅ | H | H |
| 82 | S | C₂H₅ | CH₃ | F | H |
| 83 | S | n-C₃H₇ | CH₃ | F | H |
| 84 | S | n-C₄H₉ | CH₃ | F | H |
| 85 | S | n-C₅H₁₁ | CH₃ | F | H |
| 86 | S | n-C₆H₁₃ | CH₃ | F | H |
| 87 | S | n-C₃H₇ | C₂H₅ | F | H |
| 88 | S | n-C₄H₉ | C₂H₅ | F | H |
| 89 | S | n-C₅H₁₁ | C₂H₅ | F | H |
| 90 | S | n-C₆H₁₃ | C₂H₅ | F | H |
| 91 | S | C₂H₅ | CH₃ | F | F |
| 92 | S | n-C₃H₇ | CH₃ | F | F |
| 92 | S | n-C₄H₉ | CH₃ | F | F |
| 94 | S | n-C₅H₁₁ | CH₃ | F | F |
| 95 | S | n-C₆H₁₃ | CH₃ | F | F |
| 96 | S | n-C₃H₇ | C₂H₅ | F | F |
| 97 | S | n-C₄H₉ | C₂H₅ | F | F |
| 98 | S | n-C₅H₁₁ | C₂H₅ | F | F |
| 99 | S | n-C₆H₁₃ | C₂H₅ | F | F |
| 100 | R | C₂H₅ | CH₃ | H | H |
| 101 | R | n-C₃H₇ | CH₃ | H | H |
| 102 | R | n-C₄H₉ | CH₃ | H | H |
| 103 | R | n-C₅H₁₁ | CH₃ | H | H |
| 104 | R | n-C₆H₁₃ | CH₃ | H | H |
| 105 | R | n-C₃H₇ | C₂H₅ | H | H |
| 106 | R | n-C₄H₉ | C₂H₅ | H | H |
| 107 | R | n-C₅H₁₁ | C₂H₅ | H | H |
| 108 | R | n-C₆H₁₃ | C₂H₅ | H | H |
| 109 | R | C₂H₅ | CH₃ | F | H |
| 110 | R | n-C₃H₇ | CH₃ | F | H |
| 111 | R | n-C₄H₉ | CH₃ | F | H |
| 112 | R | n-C₅H₁₁ | CH₃ | F | H |
| 113 | R | n-C₆H₁₃ | CH₃ | F | H |
| 114 | R | n-C₃H₇ | C₂H₅ | F | H |
| 115 | R | n-C₄H₉ | C₂H₅ | F | H |
| 116 | R | n-C₅H₁₁ | C₂H₅ | F | H |
| 117 | R | n-C₆H₁₃ | C₂H₅ | F | H |
| 118 | R | C₂H₅ | CH₃ | F | F |
| 119 | R | n-C₃H₇ | CH₃ | F | F |
| 129 | R | n-C₄H₉ | CH₃ | F | F |
| 121 | R | n-C₅H₁₁ | CH₃ | F | F |
| 122 | R | n-C₆H₁₃ | CH₃ | F | F |
| 123 | R | n-C₃H₇ | C₂H₅ | F | F |
| 124 | R | n-C₄H₉ | C₂H₅ | F | F |

-continued

| No. | Config.§ | R¹¹ | R¹² | X | Y |
|---|---|---|---|---|---|
| 125 | R | n-C₅H₁₁ | C₂H₅ | F | F |
| 126 | R | n-C₆H₁₃ | C₂H₅ | F | F |

Note:
§Configuration of the alcohol employed.

Examples 127 to 180

The following are prepared analogously to Example 1:

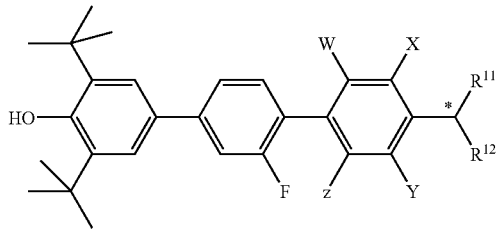

where W and Z denote H.

| No. | Config.§ | R¹¹ | R¹² | X | Y |
|---|---|---|---|---|---|
| 127 | S | C₂H₅ | CH₃ | H | H |
| 128 | S | n-C₃H₇ | CH₃ | H | H |
| 129 | S | n-C₄H₉ | CH₃ | H | H |
| 130 | S | n-C₅H₁₁ | CH₃ | H | H |
| 131 | S | n-C₆H₁₃ | CH₃ | H | H |
| 132 | S | n-C₃H₇ | C₂H₅ | H | H |
| 133 | S | n-C₄H₉ | C₂H₅ | H | H |
| 134 | S | n-C₅H₁₁ | C₂H₅ | H | H |
| 135 | S | n-C₆H₁₃ | C₂H₅ | H | H |
| 136 | S | C₂H₅ | CH₃ | F | H |
| 137 | S | n-C₃H₇ | CH₃ | F | H |
| 138 | S | n-C₄H₉ | CH₃ | F | H |
| 139 | S | n-C₅H₁₁ | CH₃ | F | H |
| 140 | S | n-C₆H₁₃ | CH₃ | F | H |
| 141 | S | n-C₃H₇ | C₂H₅ | F | H |
| 142 | S | n-C₄H₉ | C₂H₅ | F | H |
| 143 | S | n-C₅H₁₁ | C₂H₅ | F | H |
| 144 | S | n-C₆H₁₃ | C₂H₅ | F | H |
| 145 | S | C₂H₅ | CH₃ | F | F |
| 146 | S | n-C₃H₇ | CH₃ | F | F |
| 147 | S | n-C₄H₉ | CH₃ | F | F |
| 148 | S | n-C₅H₁₁ | CH₃ | F | F |
| 149 | S | n-C₆H₁₃ | CH₃ | F | F |
| 150 | S | n-C₃H₇ | C₂H₅ | F | F |
| 151 | S | n-C₄H₉ | C₂H₅ | F | F |
| 152 | S | n-C₅H₁₁ | C₂H₅ | F | F |
| 153 | S | n-C₆H₁₃ | C₂H₅ | F | F |
| 154 | R | C₂H₅ | CH₃ | H | H |
| 155 | R | n-C₃H₇ | CH₃ | H | H |
| 156 | R | n-C₄H₉ | CH₃ | H | H |
| 157 | R | n-C₅H₁₁ | CH₃ | H | H |
| 158 | R | n-C₆H₁₃ | CH₃ | H | H |
| 159 | R | n-C₃H₇ | C₂H₅ | H | H |
| 160 | R | n-C₄H₉ | C₂H₅ | H | H |
| 161 | R | n-C₅H₁₁ | C₂H₅ | H | H |
| 162 | R | n-C₆H₁₃ | C₂H₅ | H | H |
| 163 | R | C₂H₅ | CH₃ | F | H |
| 164 | R | n-C₃H₇ | CH₃ | F | H |
| 165 | R | n-C₄H₉ | CH₃ | F | H |
| 166 | R | n-C₅H₁₁ | CH₃ | F | H |
| 167 | R | n-C₆H₁₃ | CH₃ | F | H |
| 168 | R | n-C₃H₇ | C₂H₅ | F | H |
| 169 | R | n-C₄H₉ | C₂H₅ | F | H |
| 170 | R | n-C₅H₁₁ | C₂H₅ | F | H |
| 171 | R | n-C₆H₁₃ | C₂H₅ | F | H |
| 172 | R | C₂H₅ | CH₃ | F | F |
| 173 | R | n-C₃H₇ | CH₃ | F | F |
| 174 | R | n-C₄H₉ | CH₃ | F | F |
| 175 | R | n-C₅H₁₁ | CH₃ | F | F |
| 176 | R | n-C₆H₁₃ | CH₃ | F | F |
| 177 | R | n-C₃H₇ | C₂H₅ | F | F |
| 178 | R | n-C₄H₉ | C₂H₅ | F | F |
| 179 | R | n-C₅H₁₁ | C₂H₅ | F | F |
| 180 | R | n-C₆H₁₃ | C₂H₅ | F | F |

Note:
§Configuration of the alcohol employed.

Use Examples

The properties of the compounds according to the invention are investigated. To this end, liquid-crystal mixtures are prepared, and the corresponding compounds are added.

Use Example 1

A nematic liquid-crystal mixture (M0) having the following composition and physical properties is prepared.

| Compound/ abbreviation | Concentration/ % by weight | Physical properties |
|---|---|---|
| PCH-5F | 8.0 | Clearing point (N, I) = 80.5° C. |
| PCH-6F | 6.4 | |
| PCH-7F | 4.8 | |
| CCP-2OCF₃ | 6.4 | |
| CCP-3OCF₃ | 9.6 | |
| CCP-4OCF₃ | 5.6 | |
| CCP-5OCF₃ | 8.8 | |
| BCH-3F.F | 9.6 | |
| BCH-5F.F | 8.0 | |
| ECCP-3OCF₃ | 4.0 | |
| ECCP-3OCF₃ | 4.0 | |
| CC-4-V | 20.0 | |
| CBC-33F | 1.6 | |
| CBC-53F | 1.6 | |
| CBC-55F | 1.6 | |
| Σ | 100.0 | |

0.5% of the compound of Example 1 are added to this liquid-crystal mixture (M0). The clearing point of the mixture (M1) drops to 78.6° C. This doped mixture, M1, is heated in an open capillary tube (Mettler ME-18 552) at a fill level of 1 cm, at 150° C. in the presence of atmospheric oxygen. After the pre-specified times, the clearing point of the sample is determined in the capillary tube. The capillary tube is then re-heated to 150° C. For comparison, the same investigation is carried out on the undoped mixture, M0. The results of this investigation are shown in the following table.

| Mixture | M0 | M1 |
|---|---|---|
| c(B1)/% | 0 | 0.5 |
| \|P\|/μm | ∞* | 74 |
| HTP/μm$^{-1}$ | n.a. | 2.7 |
| t/h | T(N, I)/° C. | |
| 0 | 80.5 | 78.6 |
| 1 | 79.4 | 78.9 |
| 2 | 79.5 | 78.8 |
| 5 | 76.8 | 78.8 |
| 10 | 74.0 | 78.9 |
| 30 | 63.7 | 78.7 |
| 50 | 59.9 | 78.4 |

Notes:
*cannot be determined
n.a. not applicable.

The measurement accuracy in the determination of the clearing point was +/−0.3 degree.

Mixture M1 has excellent technical properties and is distinguished, in particular, by very good thermal stability, in particular in the presence of atmospheric oxygen.

In the case of the undoped mixture (M0), the clearing point drops by more than twenty differential degrees over the course of somewhat more than four days in the stability test described above. By contrast, the clearing point of the mixture according to the invention drops only insignificantly, by 0.2 differential degree.

Comparative Example C1

0.5% of the chiral dopant S-811 from Merck KGaA are added to the mixture, M0, described under Use Example 1. The resultant mixture, C1, has a clearing point of 79.0° C. and a cholesteric pitch of 17 μm. Under the thermal load described under Use Example 1, the clearing point of the mixture C1 drops significantly to 60.0° C. within 50 h.

Comparative Example C2

0.5% of the Achiral Phenol AP

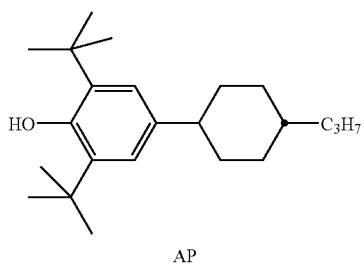

AP from DE 195 391 41 having a melting point of 91° C. are added to the mixture, M0, described under Use Example 1. The resultant mixture, C2, has a clearing point of 78.2° C. Under the thermal load described under Use Example 1, the clearing point of mixture C2 drops only insignificantly, to 78.0° C. Since the added compound is achiral, mixture C2 is likewise not chiral and thus has no cholesteric pitch.

These results are shown in the following table.

| Example | —/— | Comparative Examples 1 and 2 | | Use Example 1 |
|---|---|---|---|---|
| Mixture | M0 | C1 | C2 | M1 |
| Dopant | —/— | S-811 | AP | B1 |
| \|P\|/μm | ∞* | 17 | ∞* | 74 |
| ΔT$^§$/° | 20.6 | 19.0 | 0.2 | 0.2 |

Notes:
*cannot be determined,
$^§$ΔT = T(N, I), (50 h) − T(N, I), (0 h)

The invention claimed is:
1. A compound of formula I

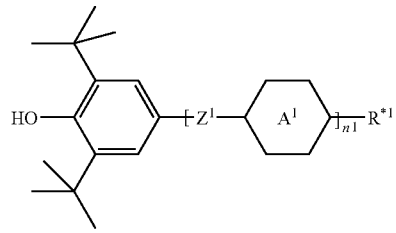

I in which
R*$^1$ is a chiral radical,
Z$^1$ is, if present more than once, in each case, independently of one another, —CH$_2$—CH$_2$—, —CH═CH—, —C≡C—, —COO—, —OCO—, —CH$_2$O—, —OCH$_2$—, —CF$_2$O—, —OCF$_2$—, —(CH$_2$)$_4$—, —CF═CF—, —CH═CF—, —CF═CH—, —CH$_2$—, —CF$_2$—, —CHF—, —O—, —S— or a single bond,

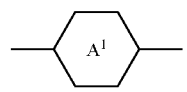

is, if present more than once, in each case, independently of one another,
(a) a trans-1,4-cyclohexylene radical, in which one or more non-adjacent CH$_2$ groups are optionally replaced by —O— and/or —S—,
(b) a 1,4-cyclohexenylene radical,
(c) a 1,4-phenylene radical, in which one or two CH groups are optionally replaced by N, or
(d) 1,4-bicyclo[2.2.2]octylene, piperidine-1,4-diyl, naphthalene-2,6-diyl, decahydronaphthalene-2,6-diyl, or 1,2,3,4-tetrahydronaphthalene-2,6-diyl,
where these radicals (a) to (d) and the phenolic benzene ring is optionally mono- or polysubstituted by F atoms, and
n$^1$ is 1, 2 or 3,
wherein
A)
R*$^1$ is a chiral radical of the following formula

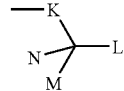

in which

K is a single bond, alkylene having 1 to 9 C atoms, alkenylene or alkynylene having 2 to 9 C atoms, wherein one, two or more of the —CH$_2$— groups present in the alkylene, alkenylene or alkynylene are optionally replaced by —O—, —C=O— or —S—, but where no two O atoms are bonded directly to one another, and the alkylene, alkenylene or alkynylene are optionally substituted by halogen, or R*$^1$ is

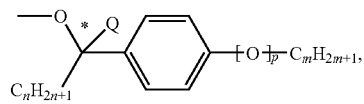

Q is H or halogen, n and m are different from one another and, independently of one another, are 1 to 11, p is 0 or 1, and L, M and N, each, independently of one another, but differently from one another and from

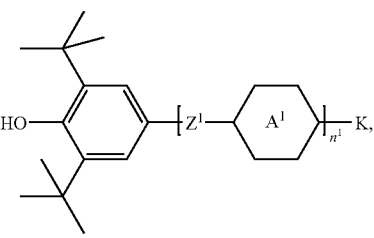

are hydrogen, halogen, aryl or cycloalkyl, alkyl or alkoxy having 1 to 11 C atoms, alkenyl, alkenyloxy, alkynyl or alkynyloxy having 2 to 11 C atoms, where one, two or more of the —CH$_2$— groups present in the alkyl, alkoxy, alkenyl, alkenyloxy, alkynyl or alkynyloxy are optionally replaced by —O—, —C=O— or —S—, but where no two O atoms are bonded directly to one another and the alkyl, alkoxy, alkenyl, alkenyloxy, alkynyl or alkynyloxy are optionally substituted by halogen;

or

B)

R*$^1$ is a chiral radical of one of the following formulae

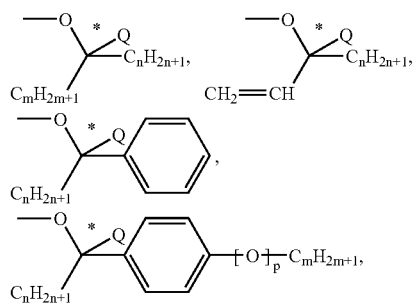

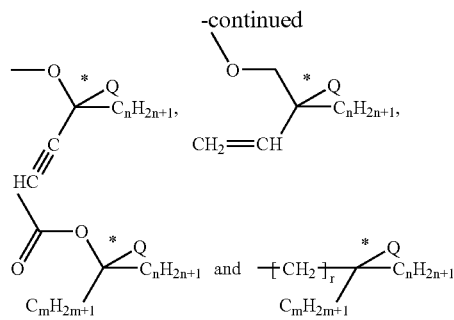

in which

Q is H or halogen, n and m are different from one another and, independently of one another, are 1 to 11, p is 0 or 1, and r is 0 to 4.

2. A compound according to claim 1, which is capable of inducing a cholesteric phase in a nematic liquid crystal and simultaneously acting as a stabiliser.

3. A compound according to claim 1, which is capable of acting as a free-radical scavenger.

4. A compound of formula Ia

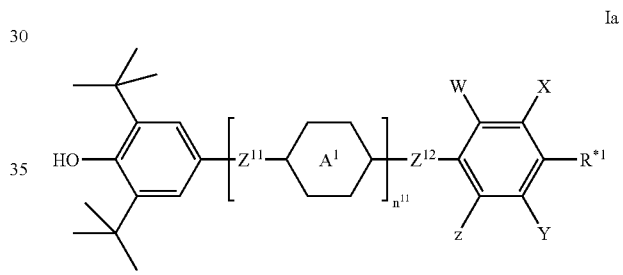

in which

is, if present more than once, in each case, independently of one another, (a) a trans-1,4-cyclohexylene radical, in which one or more non-adjacent CH$_2$ groups are optionally replaced by —O— and/or —S—, (b) a 1,4-cyclohexenylene radical, (c) a 1,4-phenylene radical, in which one or two CH groups are optionally replaced by N, or (d) 1,4-bicyclo[2.2.2]octylene, piperidine-1,4-diyl, naphthalene-2,6-diyl, decahydronaphthalene-2,6-diyl, or 1,2,3,4-tetrahydronaphthalene-2,6-diyl, where these radicals (a) to (d) and the phenolic benzene ring is optionally mono- or polysubstituted by F atoms, R*$^1$ is a chiral radical, Z$^{11}$ and Z$^{12}$ are, each independently, and in case if Z$^{11}$ present more than once, in each case, independently of one another, —CH$_2$—CH$_2$—, —CH=CH—, —C≡C—, —COO—, —OCO—, —CH$_2$O—, —OCH$_2$—, —CF$_2$O—, —OCF$_2$—, —(CH$_2$)$_4$—, —CF=CF—, —CH=CF—, —CF=CH—, —CH$_2$—, —CF$_2$—, —CHF—, —O—, —S— or a single bond, $n^{11}$ is 0, 1 or 2, W and Z are each, independently of one another, H, F, Cl, or alkoxy, and X and Y are each, independently of one another, H, F, Cl, alkyl or alkoxy, wherein

A)

the compound of formula Ia is

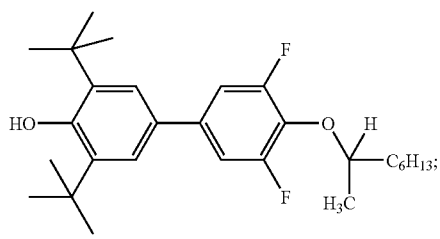

or

B)

R*$^1$ is a chiral radical of the following formula

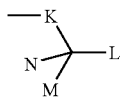

in which

K is a single bond, alkylene having 1 to 9 C atoms, alkenylene or alkynylene having 2 to 9 C atoms, wherein one, two or more of the —CH$_2$— groups present in the alkylene, alkenylene or alkynylene are optionally replaced by —O—, —C=O— or —S—, but where no two O atoms are bonded directly to one another, and the alkylene, alkenylene or alkynylene are optionally substituted by halogen, or R*$^1$ is

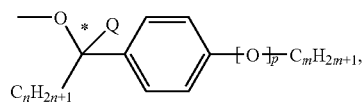

Q is H or halogen, n and m are different from one another and, independently of one another, are 1 to 11, p is 0 or 1, and L, M and N, each, independently of one another, but differently from one another and from

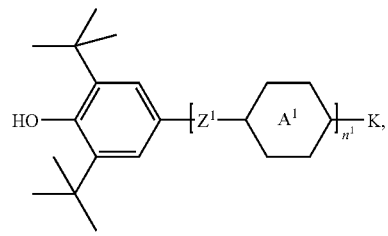

are hydrogen, halogen, aryl or cycloalkyl, alkyl or alkoxy having 1 to 11 C atoms, alkenyl, alkenyloxy, alkynyl or alkynyloxy having 2 to 11 C atoms, where one, two or more of the —CH$_2$— groups present in the alkyl, alkoxy, alkenyl, alkenyloxy, alkynyl or alkynyloxy are optionally replaced by —O—, —C=O— or —S—, but where no two O atoms are bonded directly to one another and the alkyl, alkoxy, alkenyl, alkenyloxy, alkynyl or alkynyloxy are optionally substituted by halogen;

Or

C)

R*$^1$ is a chiral radical of one of the following formulae

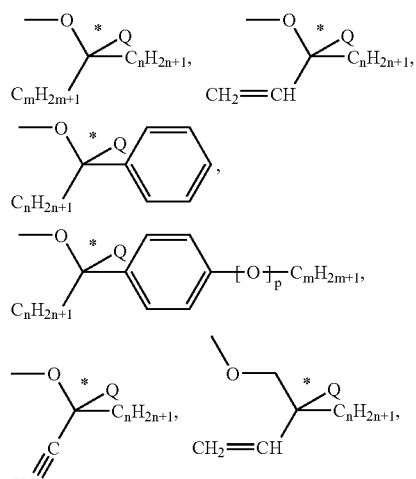

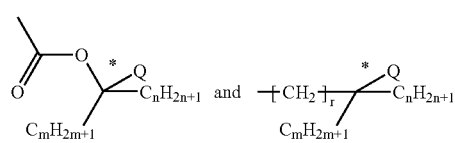

in which

Q is H or halogen, n and m are different from one another and, independently of one another, are 1 to 11, p is 0 or 1, and r is 0 to 4, and wherein one of the following conditions I, II, III, IV or V must be satisfied I) wherein the compound is

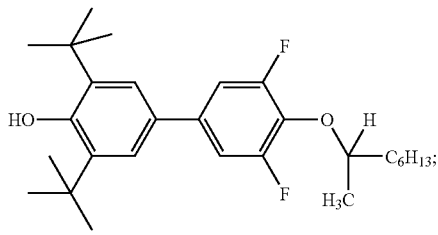

or

II) wherein
R*¹ is a chiral radical of the following formula

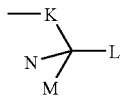

in which
K is a single bond, alkylene having 1 to 9 C atoms, alkenylene or alkynylene having 2 to 9 C atoms, wherein one, two or more of the —CH₂— groups present in the alkylene, alkenylene or alkynylene are optionally replaced by —O—, —C=O— or —S—, but where no two O atoms are bonded directly to one another, and the alkylene, alkenylene or alkynylene are optionally substituted by halogen, or
R*¹ is

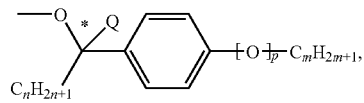

Q is H or halogen,
n and m are different from one another and, independently of one another, are 1 to 11,
p is 0 or 1, and
L, M and N, each, independently of one another, but differently from one another and from

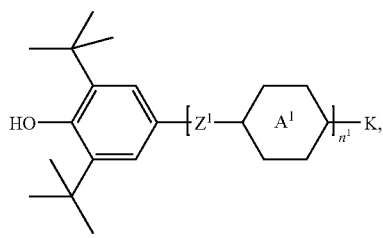

are hydrogen, halogen, aryl or cycloalkyl, alkyl or alkoxy having 1 to 11 C atoms, alkenyl, alkenyloxy, alkynyl or alkynyloxy having 2 to 11 C atoms, where one, two or more of the —CH₂— groups present in the alkyl, alkoxy, alkenyl, alkenyloxy, alkynyl or alkynyloxy are optionally replaced by —O—, —CO— or —S—, but where no two O atoms are bonded directly to one another and the alkyl, alkoxy, alkenyl, alkenyloxy, alkynyl or alkynyloxy are optionally substituted by halogen;

or

III) wherein
R*¹ is a chiral radical of one of the following formulae

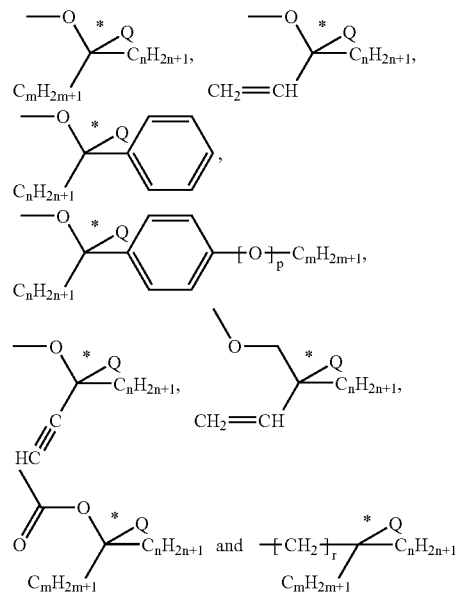

in which
Q is H or halogen,
n and m are different from one another and, independently of one another, are 1 to 11,
p is 0 or 1, and
r is 0 to 4;

or

IV) wherein
W and Z are each, independently of one another, H, F or Cl;

or

V) wherein
W and Z are both H.

5. A compound according to claim 1, wherein
R*¹ is a chiral radical of the following formula

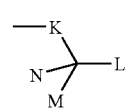

in which
K is a single bond, alkylene having 1 to 9 C atoms, alkenylene or alkynylene having 2 to 9 C atoms, wherein one, two or more of the —CH₂— groups present in the alkylene, alkenylene or alkynylene are optionally replaced by —O—, —C=O— or —S—, but where no two O atoms are bonded directly to one another, and the alkylene, alkenylene or alkynylene are optionally substituted by halogen, or R*¹ is

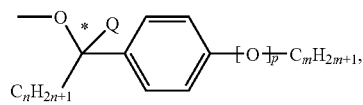

Q is H or halogen, n and m are different from one another and, independently of one another, are 1 to 11, p is 0 or 1, and L, M and N, each, independently of one another, but differently from one another and from

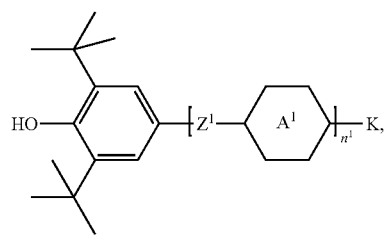

are hydrogen, halogen, aryl or cycloalkyl, alkyl or alkoxy having 1 to 11 C atoms, alkenyl, alkenyloxy, alkynyl or alkynyloxy having 2 to 11 C atoms, where one, two or more of the —CH₂— groups present in the alkyl, alkoxy, alkenyl, alkenyloxy, alkynyl or alkynyloxy are optionally replaced by —O—, —C=O— or —S—, but where no two O atoms are bonded directly to one another and the alkyl, alkoxy, alkenyl, alkenyloxy, alkynyl or alkynyloxy are optionally substituted by halogen.

6. A compound according to claim 1, wherein

R*¹ is a chiral radical of one of the following formulae

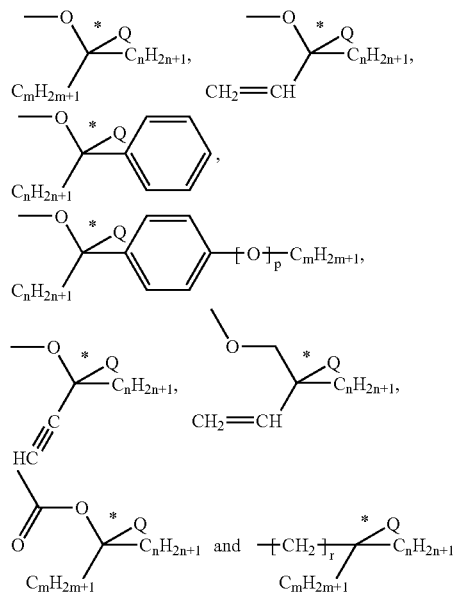

in which

Q is H or halogen, n and m are different from one another and, independently of one another, are 1 to 11, p is 0 or 1, and r is 0 to 4.

7. A compound of formula Ia-2, Ia-3, Ia-4, Ia-5, Ia-6, Ia-7, Ia-8, or Ia-9

Ia-2

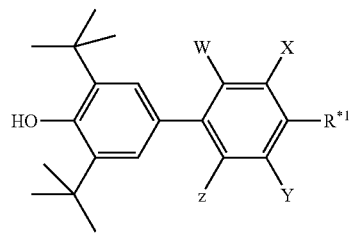

Ia-3

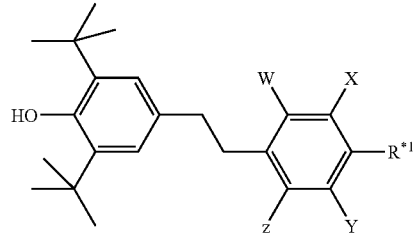

Ia-4

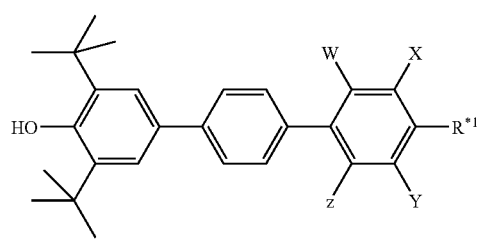

Ia-5

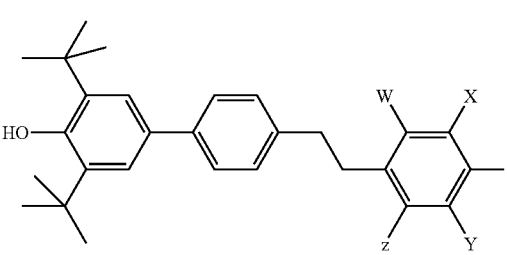

Ia-6

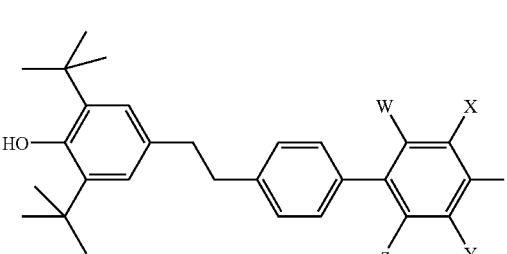

-continued

Ia-7

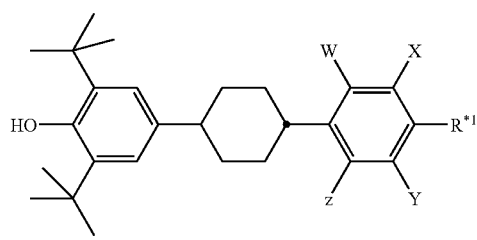

Ia-8

Ia-9 wherein
W, X, Y and Z are each, independently of one another, H, F, Cl, alkyl or alkoxy,
R*¹ is a chiral radical;
wherein
A)
R*¹ is a chiral radical of the following formula

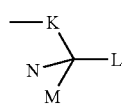

in which
K is a single bond, alkylene having 1 to 9 C atoms, alkenylene or alkynylene having 2 to 9 C atoms, wherein one, two or more of the —CH$_2$— groups present in the alkylene, alkenylene or alkynylene are optionally replaced by —O—, —C═O— or —S—, but where no two O atoms are bonded directly to one another, and the alkylene, alkenylene or alkynylene are optionally substituted by halogen, or
R*¹ is

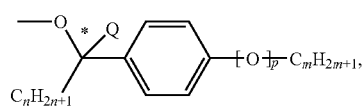

Q is H or halogen,
n and m are different from one another and, independently of one another, are 1 to 11,
p is 0 or 1, and
L, M and N, each, independently of one another, but differently from one another and from are hydrogen, halogen, aryl or cycloalkyl, alkyl or alkoxy having 1 to 11 C atoms, alkenyl, alkenyloxy, alkynyl or alkynyloxy having 2 to 11 C atoms, where one, two or more of the —CH$_2$— groups present in the alkyl, alkoxy, alkenyl, alkenyloxy, alkynyl or alkynyloxy are optionally replaced by —O—, —C═O— or —S—, but where no two O atoms are bonded directly to one another and the alkyl, alkoxy, alkenyl, alkenyloxy, alkynyl or alkynyloxy are optionally substituted by halogen;
or
B)
R*¹ is a chiral radical of one of the following formulae in which
Q is H or halogen,
n and m are different from one another and, independently of one another, are 1 to 11,
p is 0 or 1, and
r is 0 to 4.
8. A method of providing a chiral dopant, or a stabiliser, or a chiral dopant and simultaneously a stabiliser to a liquid crystal mixture, comprising adding a compounds according to claim 1 to said liquid crystal mixture.

9. A liquid-crystal medium comprising a compound according to claim 1.

10. An electro-optical display comprising a liquid-crystal medium which comprises a compound according to claim 1.

11. A process for preparing a liquid-crystal mixture, comprising mixing together a compound of formula I according to claim 1 with one or more liquid-crystal compounds other than a compound of formula I to form a liquid-crystal mixture.

12. A compound according to claim 4, which is

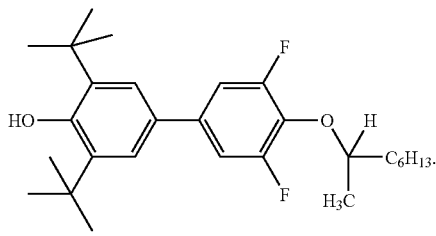

13. A compound according to claim 4, wherein R*¹ is a chiral radical of the following formula

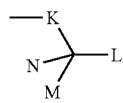

in which
K is a single bond, alkylene having 1 to 9 C atoms, alkenylene or alkynylene having 2 to 9 C atoms, wherein one, two or more of the —CH$_2$— groups present in the alkylene, alkenylene or alkynylene are optionally replaced by —O—, —C=O— or —S—, but where no two O atoms are bonded directly to one another, and the alkylene, alkenylene or alkynylene are optionally substituted by halogen, or
R*¹ is

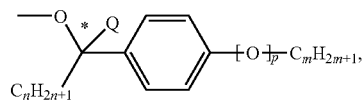

Q is H or halogen,
n and m are different from one another and, independently of one another, are 1 to 11,
p is 0 or 1, and
L, M and N, each, independently of one another, but differently from one another and from are hydrogen, halogen, aryl or cycloalkyl, alkyl or alkoxy having 1 to 11 C atoms, alkenyl, alkenyloxy, alkynyl or alkynyloxy having 2 to 11 C atoms, where one, two or more of the —CH$_2$— groups present in the alkyl, alkoxy, alkenyl, alkenyloxy, alkynyl or alkynyloxy are optionally replaced by —O—, —C=O— or —S—, but where no two O atoms are bonded directly to one another and the alkyl, alkoxy, alkenyl, alkenyloxy, alkynyl or alkynyloxy are optionally substituted by halogen.

14. A compound according to claim 4, wherein R*¹ is a chiral radical of one of the following formulae

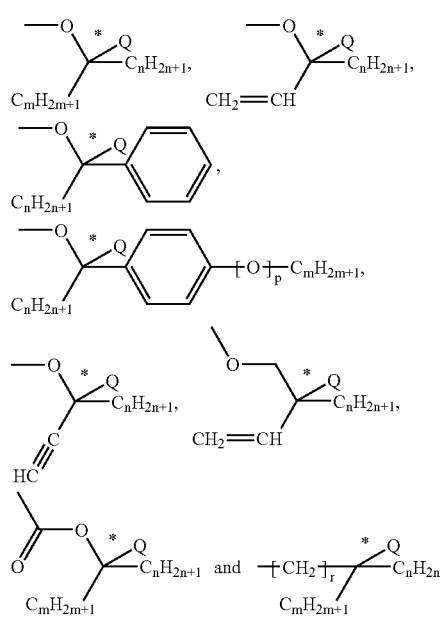

in which
Q is H or halogen,
n and m are different from one another and, independently of one another, are 1 to 11,
p is 0 or 1, and
r is 0 to 4.

15. A compound according to claim 4, wherein W and Z are each, independently of one another, H, F or Cl.

16. A compound according to claim 4, wherein W and Z are both H.

17. A compound of formula I

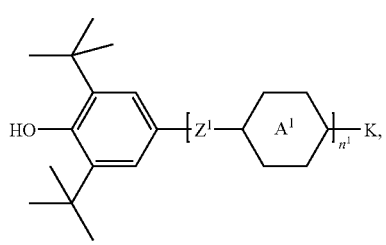
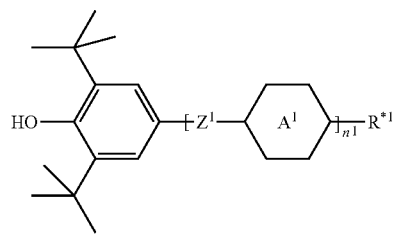

in which

R*¹ is a chiral radical of the following formula

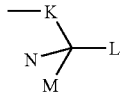

in which

K is a single bond, alkylene having 1 to 9 C atoms, alkenylene or alkynylene having 2 to 9 C atoms, wherein one, two or more of the —CH₂— groups present in the alkylene, alkenylene or alkynylene are optionally replaced by —O—, —C═O— or —S—, but where no two O atoms are bonded directly to one another, and the alkylene, alkenylene or alkynylene are optionally substituted by halogen, or R*¹ is a group

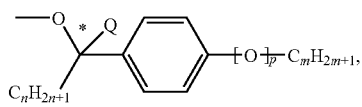

Q is H or halogen, n and m are different from one another and, independently of one another, are 1 to 11, p is 0 or 1, L, M and N, each, independently of one another, but differently from one another and from

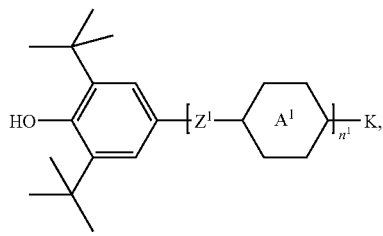

are hydrogen, halogen, aryl or cycloalkyl, alkyl or alkoxy having 1 to 11 C atoms, alkenyl, alkenyloxy, alkynyl or alkynyloxy having 2 to 11 C atoms, where one, two or more of the —CH₂— groups present in the alkyl, alkoxy, alkenyl, alkenyloxy, alkynyl or alkynyloxy are optionally replaced by —O—, —C═O— or —S—, but where no two O atoms are bonded directly to one another and the alkyl, alkoxy, alkenyl, alkenyloxy, alkynyl or alkynyloxy are optionally substituted by halogen, Z¹ is, if present more than once, in each case, independently of one another, —CH₂—CH₂—, —CH═CH—, —C≡C—, —COO—, —OCO—, —CH₂O—, —OCH₂—, —CF₂O—, —OCF₂—, —(CH₂)₄—, —CF═CF—, —CH═CF—, —CF═CH—, —CH₂—, —CF₂—, —CHF—, —O—, —S— or a single bond,

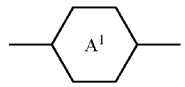

is, if present more than once, in each case, independently of one another, (a) a trans-1,4-cyclohexylene radical, in which one or more non-adjacent CH₂ groups are optionally replaced by —O— and/or —S—, (b) a 1,4-cyclohexenylene radical, (c) a 1,4-phenylene radical, in which one or two CH groups are optionally replaced by N, or (d) 1,4-bicyclo[2.2.2]octylene, piperidine-1,4-diyl, naphthalene-2,6-diyl, decahydronaphthalene-2,6-diyl, or 1,2,3,4-tetrahydronaphthalene-2,6-diyl, where these radicals (a) to (d) and the phenolic benzene ring is optionally mono- or polysubstituted by F atoms, and n¹ is 1, 2 or 3.

18. A compound according to claim 17, wherein

R*¹ is a chiral radical of one of the following formulae

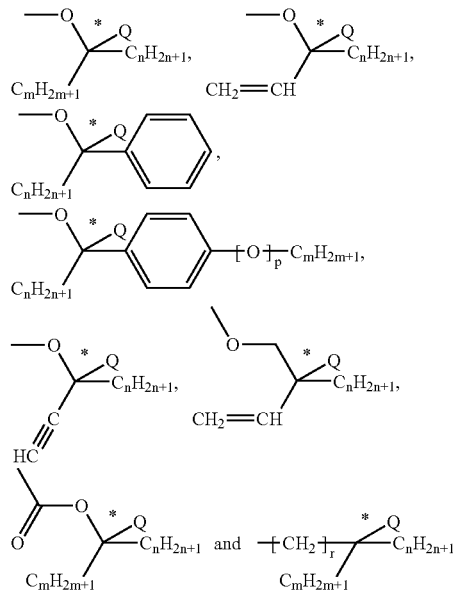

in which

Q is H or halogen, n and m are different from one another and, independently of one another, are 1 to 11, p is 0 or 1, and r is 0 to 4.

19. A compound according to claim 7, wherein

R*¹ is a chiral radical of the following formula

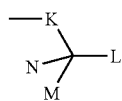

in which

K is a single bond, alkylene having 1 to 9 C atoms, alkenylene or alkynylene having 2 to 9 C atoms, wherein one, two or more of the —CH$_2$— groups present in the alkylene, alkenylene or alkynylene are optionally replaced by —O—, —C═O— or —S—, but where no two O atoms are bonded directly to one another, and the alkylene, alkenylene or alkynylene are optionally substituted by halogen, or R*$^1$ is

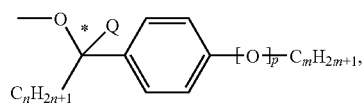

Q is H or halogen, n and m are different from one another and, independently of one another, are 1 to 11, p is 0 or 1, and L, M and N, each, independently of one another, but differently from one another and from

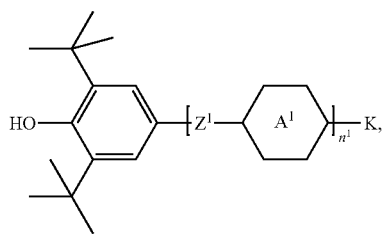

are hydrogen, halogen, aryl or cycloalkyl, alkyl or alkoxy having 1 to 11 C atoms, alkenyl, alkenyloxy, alkynyl or alkynyloxy having 2 to 11 C atoms, where one, two or more of the —CH$_2$— groups present in the alkyl, alkoxy, alkenyl, alkenyloxy, alkynyl or alkynyloxy are optionally replaced by —O—, —C═O— or —S—, but where no two O atoms are bonded directly to one another and the alkyl, alkoxy, alkenyl, alkenyloxy, alkynyl or alkynyloxy are optionally substituted by halogen.

20. A compound according to claim 7, wherein

R*$^1$ is a chiral radical of one of the following formulae

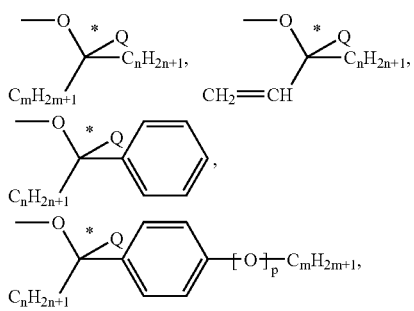

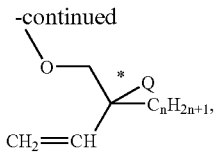

-continued

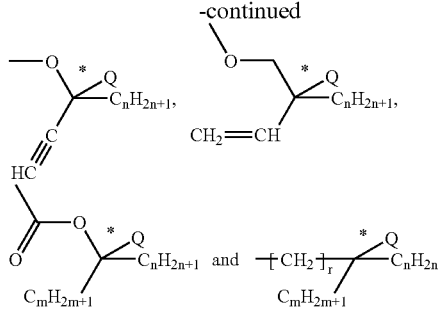

in which

Q is H or halogen, n and m are different from one another and, independently of one another, are 1 to 11, p is 0 or 1, and r is 0 to 4.

21. A compound according to claim 5, wherein K is a single bond, —CH$_2$—, —O—, —CO—O—, —CO—O—CH$_2$—, —O—CO—, —CH$_2$—CH$_2$—, —CH═CH— or —C≡C—.

22. A compound according to claim 13, wherein K is a single bond, —CH$_2$—, —O—, —CO—O—, —CO—O—CH$_2$—, —O—CO—, —CH$_2$—CH$_2$—, —CH═CH— or —C≡C—.

23. A compound according to claim 5, wherein

L, M and N are each, independently of one another, hydrogen, halogen, alkyl or alkoxy having 1 to 11 C atoms, alkenyl, alkenyloxy, alkynyl or alkynyloxy having 2 to 11 C atoms, where one, two or more of the —CH$_2$— groups present are optionally replaced by —O—, —C═O— or —S—, but where no two O atoms are bonded directly to one another, and are optionally substituted by halogen.

24. A compound according to claim 13, wherein

L, M and N are each, independently of one another, hydrogen, halogen, alkyl or alkoxy having 1 to 11 C atoms, alkenyl, alkenyloxy, alkynyl or alkynyloxy having 2 to 11 C atoms, where one, two or more of the —CH$_2$— groups present are optionally replaced by —O—, —C═O— or —S—, but where no two O atoms are bonded directly to one another, and are optionally substituted by halogen.

25. A compound according to claim 23, wherein

L, M and N are each, independently of one another, hydrogen, halogen, alkyl or alkoxy having 1 to 11 C atoms, alkenyl, alkenyloxy, alkynyl or alkynyloxy having 2 to 11 C atoms.

26. A compound according to claim 24, wherein

L, M and N are each, independently of one another, hydrogen, halogen, alkyl or alkoxy having 1 to 11 C atoms, alkenyl, alkenyloxy, alkynyl or alkynyloxy having 2 to 11 C atoms.

27. A method of providing a chiral dopant, or a stabiliser, or a chiral dopant and simultaneously a stabiliser to a liquid crystal mixture, comprising adding to said liquid crystal mixture a compound according to claim 4.

28. An electro-optical display comprising a liquid-crystal medium comprising a compound according to claim 4.

29. An electro-optical display comprising a liquid-crystal medium which comprises a compound according to claim 7.

30. A liquid crystal mixture containing at least two liquid crystalline compounds one of which is a compound of formula Ia Ia

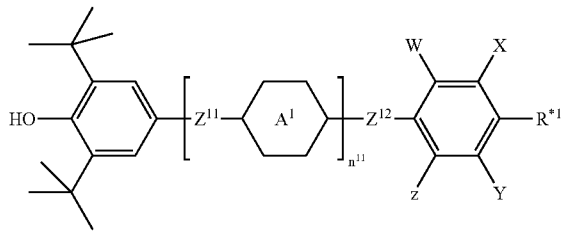

in which

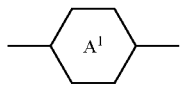

is, if present more than once, in each case, independently of one another,
(a) a trans-1,4-cyclohexylene radical, in which one or more non-adjacent CH$_2$ groups are optionally replaced by —O— and/or —S—,
(b) a 1,4-cyclohexenylene radical,
(c) a 1,4-phenylene radical, in which one or two CH groups are optionally replaced by N, or
(d) 1,4-bicyclo[2.2.2]octylene, piperidine-1,4-diyl, naphthalene-2,6-diyl, decahydronaphthalene-2,6-diyl, or 1,2,3,4-tetrahydronaphthalene-2,6-diyl, where these radicals (a) to (d) and the phenolic benzene ring is optionally mono- or polysubstituted by F atoms,
R*$^1$ is a chiral radical,
Z$^{11}$ and Z$^{12}$ are, each independently, and in case if Z$^{11}$ present more than once, in each case, independently of one another, —CH$_2$—CH$_2$—, —CH=CH—, —C≡C—, —COO—, —OCO—, —CH$_2$O—, —OCH$_2$—, —CF$_2$O—, —OCF$_2$—, —(CH$_2$)$_4$—, —CF=CF—, —CH=CF—, —CF=CH—, —CH$_2$—, —CF$_2$—, —CHF—, —O—, —S— or a single bond,
n$^{11}$ is 0, 1 or 2,
W and Z are each, independently of one another, H, F, Cl, or alkoxy, and
X and Y are each, independently of one another, H, F, Cl, alkyl or alkoxy,
wherein
A)
the compound of formula Ia is

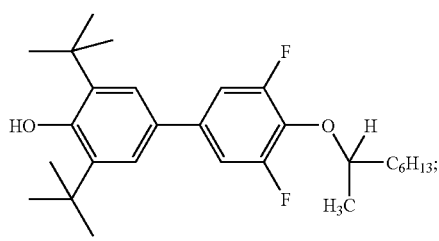

or
B)
R*$^1$ is a chiral radical of the following formula

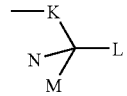

in which
K is a single bond, alkylene having 1 to 9 C atoms, alkenylene or alkynylene having 2 to 9 C atoms, wherein one, two or more of the —CH$_2$— groups present in the alkylene, alkenylene or alkynylene are optionally replaced by —O—, —C=O— or —S—, but where no two O atoms are bonded directly to one another, and the alkylene, alkenylene or alkynylene are optionally substituted by halogen, or
R*$^1$ is

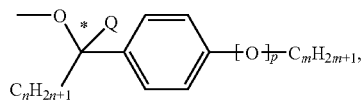

Q is H or halogen,
n and m are different from one another and, independently of one another, are 1 to 11,
p is 0 or 1, and
L, M and N, each, independently of one another, but differently from one another and from

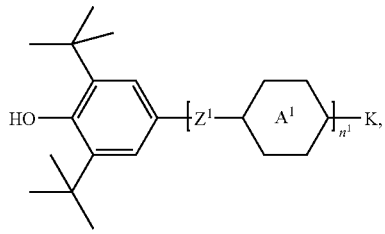

are hydrogen, halogen, aryl or cycloalkyl, alkyl or alkoxy having 1 to 11 C atoms, alkenyl, alkenyloxy, alkynyl or alkynyloxy having 2 to 11 C atoms, where one, two or more of the —CH$_2$— groups present in the alkyl, alkoxy, alkenyl, alkenyloxy, alkynyl or alkynyloxy are optionally replaced by —O—, —C=O— or —S—, but where no two O atoms are bonded directly to one another and the alkyl, alkoxy, alkenyl, alkenyloxy, alkynyl or alkynyloxy are optionally substituted by halogen;
or
C)
R*$^1$ is a chiral radical of one of the following formulae

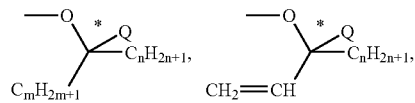

-continued
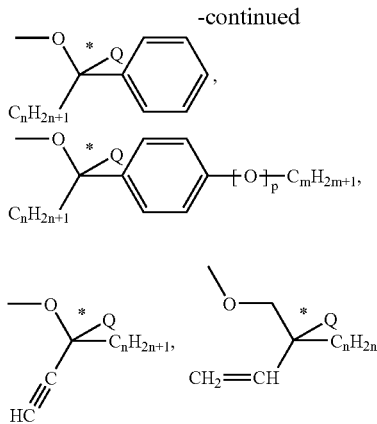
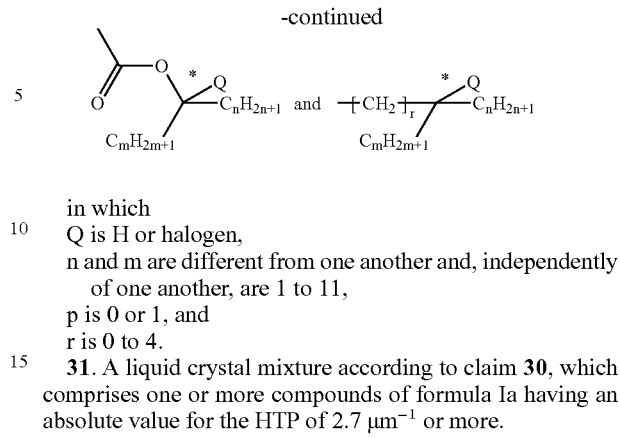
in which
Q is H or halogen,
n and m are different from one another and, independently of one another, are 1 to 11,
p is 0 or 1, and
r is 0 to 4.
31. A liquid crystal mixture according to claim 30, which comprises one or more compounds of formula Ia having an absolute value for the HTP of 2.7 $\mu m^{-1}$ or more.
* * * * *